US012765999B2

(12) United States Patent
Chen et al.

(10) Patent No.: US 12,765,999 B2
(45) Date of Patent: Oct. 20, 2026

(54) ARTIFICIAL VALVE AND VALVE DELIVERY SYSTEM

(71) Applicant: PERMED BIOMEDICAL ENGINEERING CO., LTD., Beijing (CN)

(72) Inventors: Zhuo Chen, Beijing (CN); Xiongtao Lin, Beijing (CN); Liang Zhang, Beijing (CN); Liu Yang, Beijing (CN); Feng Yin, Beijing (CN); Yi Bian, Beijing (CN)

(73) Assignee: PERMED BIOMEDICAL ENGINEERING CO., LTD., Beijing (CN)

(*) Notice: Subject to any disclaimer, the term of this patent is extended or adjusted under 35 U.S.C. 154(b) by 922 days.

(21) Appl. No.: 18/167,874

(22) Filed: Feb. 12, 2023

(65) Prior Publication Data

US 2023/0200990 A1 Jun. 29, 2023

Related U.S. Application Data

(63) Continuation of application No. PCT/CN2021/112107, filed on Aug. 11, 2021.

(30) Foreign Application Priority Data

Aug. 25, 2020 (CN) ........................ 202010867212.5

(51) Int. Cl.
*A61F 2/24* (2006.01)
*A61F 2/966* (2013.01)

(52) U.S. Cl.
CPC .......... *A61F 2/2436* (2013.01); *A61F 2/2418* (2013.01); *A61F 2002/9665* (2013.01)

(58) Field of Classification Search
CPC .................. A61F 2/2418; A61F 2/2409; A61F 2250/0039; A61F 2/2433;
(Continued)

(56) References Cited

U.S. PATENT DOCUMENTS 8,834,563 B2 * 9/2014 Righini ................ A61F 2/2436 623/2.18
2004/0111147 A1 * 6/2004 Rabkin .................. A61F 2/915 623/1.15
(Continued)

FOREIGN PATENT DOCUMENTS

CA 2905544 A1 * 9/2014 .......... A61F 2/2412
CN 102113921 7/2011
(Continued)

*Primary Examiner* — Seema Mathew
(74) *Attorney, Agent, or Firm* — JCIPRNET

(57) ABSTRACT

An artificial valve and a valve delivery system are provided. The artificial valve includes a top stent, a middle stent and a bottom stent. The top stent, the middle stent and the bottom stent are connected in sequence; the top stent is circumferentially provided with at least three locking stents; each locking stent has a locking end at the top; the middle stent is provided with at least three valve leaflet fixing parts; in the unlocked state of each locking end, the diameter of the circumference where the uppermost edges of the three valve leaflet fixing parts are located is Φ1, and in the locked state of each locking end, the diameter of the circumference where the uppermost edges of the three valve leaflet fixing parts are located is Φ2, which is larger than or equal to 74% of Φ1.

17 Claims, 32 Drawing Sheets

(58) Field of Classification Search
CPC ...... A61F 2250/0018; A61F 2250/0036; A61F 2/915; A61F 2/24; A61F 2/243; A61F 2/9517; A61F 2/9522; A61F 2240/001; A61F 2/82; A61F 2/90; A61F 2/95; A61F 2002/91525; A61F 2002/9528; A61F 2002/9534; A61F 2250/0037; A61F 2/246; A61F 2/2463; A61F 2/86; A61F 2/848; A61F 2/852; A61F 2002/823
See application file for complete search history.

(56) References Cited

U.S. PATENT DOCUMENTS

| | | | | |
|---|---|---|---|---|
| 2006/0122692 | A1* | 6/2006 | Gilad | A61F 2/2418 623/1.35 |
| 2006/0161187 | A1* | 7/2006 | Levine | A61F 5/0076 606/153 |
| 2006/0259136 | A1* | 11/2006 | Nguyen | A61F 2/2412 623/2.18 |
| 2009/0287299 | A1* | 11/2009 | Tabor | A61F 2/013 623/1.26 |
| 2010/0049303 | A1* | 2/2010 | Guyenot | A61F 2/2418 623/1.24 |
| 2010/0049313 | A1* | 2/2010 | Alon | A61F 2/2436 623/2.11 |
| 2010/0070027 | A1* | 3/2010 | Bonhoeffer | A61F 2/2409 623/2.11 |
| 2010/0249911 | A1* | 9/2010 | Alkhatib | A61F 2/2418 623/1.26 |
| 2010/0268332 | A1* | 10/2010 | Tuval | A61F 2/2436 623/2.1 |
| 2011/0098800 | A1 | 4/2011 | Braido et al. | |
| 2011/0264206 | A1* | 10/2011 | Tabor | A61F 2/2409 623/2.12 |
| 2012/0053682 | A1* | 3/2012 | Kovalsky | A61F 2/2418 623/2.11 |
| 2012/0172982 | A1* | 7/2012 | Stacchino | A61F 2/2436 623/2.17 |
| 2012/0197390 | A1* | 8/2012 | Alkhatib | A61F 2/2418 623/2.18 |
| 2014/0249622 | A1 | 9/2014 | Carmi et al. | |
| 2015/0057747 | A1* | 2/2015 | Li | A61F 2/2418 623/2.18 |
| 2015/0297381 | A1* | 10/2015 | Essinger | A61F 2/0095 623/1.26 |
| 2015/0359629 | A1* | 12/2015 | Ganesan | A61F 2/2409 623/2.14 |
| 2015/0366665 | A1 | 12/2015 | Lombardi et al. | |
| 2017/0065410 | A1 | 3/2017 | Straubinger et al. | |
| 2021/0236281 | A1 | 8/2021 | Straubinger et al. | |

FOREIGN PATENT DOCUMENTS

| | | | | | |
|---|---|---|---|---|---|
| CN | 204121202 | U | * | 1/2015 | |
| CN | 104968300 | | | 10/2015 | |
| CN | 104983485 | | | 10/2015 | |
| CN | 105496608 | | | 4/2016 | |
| CN | 105662651 | | | 6/2016 | |
| CN | 205339217 | U | * | 6/2016 | |
| CN | 107088112 | | | 8/2017 | |
| CN | 107550524 | | | 1/2018 | |
| CN | 109394393 | | | 3/2019 | |
| CN | 208910583 | | | 5/2019 | |
| CN | 212630962 | | | 3/2021 | |
| CN | 215875097 | U | * | 2/2022 | |
| CN | 114191146 | A | * | 3/2022 | A61F 2/2463 |
| WO | WO-2009053497 | A1 | * | 4/2009 | A61F 2/2436 |
| WO | WO-2010006627 | A1 | * | 1/2010 | A61F 2/2418 |
| WO | WO-2011051043 | A1 | * | 5/2011 | A61F 2/2412 |
| WO | WO-2011079803 | A1 | * | 7/2011 | A61F 2/2415 |
| WO | 2019033989 | | | 2/2019 | |
| WO | 2019119674 | | | 6/2019 | |

* cited by examiner

ARTIFICIAL VALVE AND VALVE DELIVERY SYSTEM

CROSS-REFERENCE TO RELATED APPLICATION

This application is a continuation of international application of PCT application Ser. No. PCT/CN2021/112107 filed on Aug. 11, 2021, which claims the priority benefit of China application no. 202010867212.5 filed on Aug. 25, 2020. The entirety of each of the abovementioned patent applications is hereby incorporated by reference herein and made a part of this specification.

FIELD

The present disclosure belongs to the field of medical instruments, and particularly relates to an artificial valve and a valve delivery system.

BACKGROUND

Aortic valvular disease is a common heart valve disease, and its incidence rate gradually increases with age.

At present, surgical method is usually used to replace the diseased valves of patients with artificial heart valves. However, this method is not applicable to some elderly patients suffering from problems such as comorbid diseases. For the above-mentioned patients, minimally invasive transcatheter aortic valve implantation can be used for artificial heart valve replacement. The transcatheter aortic valve implantation has received more and more attention because it does not require thoracotomy and thus has the advantages of less trauma and quicker recovery.

Since the rise of the transcatheter aortic valve implantation, various manufacturers have launched valve delivery devices with various functions, and one of the important indicators for a valve delivery device is withdraw-ability. Before the final release, the valve is usually partially released. By evaluating the hydrodynamic indicators of the partially released (pre-released) valve, it is determined whether the implantation position of the transcatheter aortic valve is appropriate. After evaluation, if the valve implantation position needs to be adjusted, the pre-released valve can be withdrawn into a sheath and rearranged to readjust the implantation position, which is known as the withdrawal operation. The withdraw-ability means that a transcatheter aortic valve device can realize the withdrawal operation.

The full-height pre-release of the valve will help doctors fully determine the working condition of the implanted valve in advance, so as to better determine the direction of subsequent adjustment of the implantation plan.

However, none of the existing valves can achieve full-height pre-release, and the valve needs to be locked and restrained with the help of a sheath during release; while during pre-release, the sheath of the device will not allow withdrawal in full-height range. Therefore, the valve cannot be completely released, which means complete withdrawal cannot be achieved. In addition, doctors cannot fully determine the working condition of the implanted valve in advance.

SUMMARY

The present disclosure aims to provide an artificial valve and a valve delivery system. The present disclosure can realize approximate full-height pre-release of a valve in locked state, which enables doctors to fully determine the working condition of the implanted valve in advance, so as to better determine the direction of the subsequent adjustment of the implantation plan.

The specific technical solutions are as follows:

The present disclosure provides an artificial valve, including a top stent, a middle stent and a bottom stent. The top stent, the middle stent and the bottom stent are connected in sequence. The top stent is circumferentially provided with at least three locking stents; and each locking stent has a locking end at the top; the middle stent is provided with at least three valve leaflet fixing parts; in the unlocked state of each locking end, the diameter of the circumference where the uppermost edges of the three valve leaflet fixing parts are located is Φ1; and in the locked state of each locking end, the diameter of the circumference where the uppermost edges of the three valve leaflet fixing parts are located is Φ2, wherein Φ2 is larger than or equal to 74% of Φ1.

In one of the embodiments, the middle stent is provided with an anchoring frame protruding circumferentially and facing the direction of the bottom stent.

In one of the embodiments, the anchoring frame includes fixed sections and free sections; the fixed sections protrude circumferentially outward relative to the middle stent; and the free sections bend circumferentially inward relative to the fixed sections.

In one of the embodiments, the anchoring frame includes two fixed sections and two free sections; the upper ends of the two fixed sections are connected to the middle stent, and the ends of the two free sections are connected.

In one of the embodiments, the ends of the two free sections are connected to form an end socket; a perforation is formed in the end socket.

In one of the embodiments, the perforation is provided with a protective sleeve and/or a developing positioning piece.

In one of the embodiments, Φ2 is 74% to 120% of Φ1.

In one of the embodiments, the structural stiffness of the top stent is smaller than that of the middle stent.

In one of the embodiments, the middle stent includes three suture rods, which are the valve leaflet fixing parts, and three locking stents are provided; the structural stiffness of the locking end of each locking stent is 5% to 50% of the structural stiffness of the suture rods.

In one of the embodiments, the middle stent includes three suture rods, which are the valve leaflet fixing parts; and six locking stents are provided, and the structural stiffness of the locking end of each locking stent is 3% to 45% of the structural stiffness of the suture rods.

In one of the embodiments, the valve leaflet fixing parts are provided with a plurality of valve leaflet fixing holes.

In one of the embodiments, the circumferential diameter of the bottom stent gradually increases toward the bottom to form a trumpet shape.

In one of the embodiments, a circumferential skirt is arranged on the bottom stent.

The present disclosure further provides an artificial valve, including a top stent, a middle stent and a bottom stent. The top stent, the middle stent and the bottom stent are connected in sequence, and the top stent is circumferentially provided with at least three locking stents, which have locking ends at the top ends; the middle stent is provided with valve leaflet fixing parts; the structural stiffness of the top stent is smaller than that of the middle stent.

In one of the embodiments, the middle stent includes three suture rods, which are the valve leaflet fixing parts; three locking stents are provided, and the structural stiffness of the locking end of each locking stent is 5% to 50% of the structural stiffness of the suture rods.

In one of the embodiments, the middle stent includes three suture rods, which are the valve leaflet fixing parts; six locking stents are provided, and the structural stiffness of the locking end of each locking stent is 3% to 45% of the structural stiffness of the suture rods.

In one of the embodiments, the middle stent further includes suture rods and connection rods, and the locking stents, the suture rods, the connection rods and the bottom stent are connected in sequence to form an integrated structure; the maximum cross-sectional area of a locking stent is 20% to 50% of the minimum cross-sectional area of a suture rod, and the cross-section is perpendicular to the central axis of the whole valve.

The present disclosure further provides an artificial valve, including a top stent, a middle stent and a bottom stent. The top stent, the middle stent and the bottom stent are connected in sequence. The top stent is circumferentially provided with at least three locking stents, which have locking ends at the top ends, and the middle stent is provided with valve leaflet fixing parts; and the middle stent further includes suture rods and connection rods, and the locking stents, the suture rods, the connection rods and the bottom stent are connected in sequence to form an integrated structure; the maximum cross-sectional area of the locking stent is 20% to 50% of the minimum cross-sectional area of the suture rod; the cross-section is perpendicular to the central axis of the whole valve.

The present disclosure further provides a valve delivery system, including an artificial valve and a delivery device, wherein the artificial valve includes a top stent, a middle stent and a bottom stent; the top stent, the middle stent and the bottom stent are connected in sequence; the top stent is circumferentially provided with at least three locking stents, and each locking stent has a locking end at the top; the middle stent is provided with at least three valve leaflet fixing parts;

the delivery device includes a first locking member, a second locking member and a sheath; the first locking member and the second locking member are relatively movable; the first locking member is provided with a first locking portion; the second locking member is provided with a second locking portion; a locking position is formed between the first locking portion and the second locking portion; the inner diameter of the sheath is larger than the radial dimension of the second locking member; and the sheath is movably sleeved on the outside of the first locking member and the second locking member; and when the first locking member and the second locking member move relatively, the locking position is in unlocked or locked state; in the unlocked state of each locking end, the diameter of the circumference where the uppermost edges of the three valve leaflet fixing parts are located is in the locked state of each locking end, the diameter of the circumference where the uppermost edges of the three valve leaflet fixing parts are located is Φ2, wherein Φ2 is 74% to 120% of Φ1.

The technical solutions provided by the present disclosure have the following advantages and effects:

In the unlocked state, the diameter of the circumference where the uppermost edges of the three valve leaflet fixing parts are located is Φ1, and the valve is in a fully working state at this time. In the full-height pre-released state when the artificial valve is implanted (the valve is completely disengaged from the sheath, but the locking ends of the locking stents are still locked together) the diameter of the circumference where the uppermost edges of the three valve leaflet fixing parts are located is Φ2, wherein Φ2 is in the range of 74% to 120% of Φ1 at the moment, which can ensure that the valve can reach the basic working state in the locked state, so that doctors can determine the working condition of the implanted valve in advance, so as to better determine the direction of subsequent adjustments to the implantation plan without completely unlocking and releasing the artificial valve. When the artificial valve does not meet the requirements, the artificial valve can be easily withdrawn.

BRIEF DESCRIPTION OF THE DRAWINGS

The drawings here show specific embodiments of the technical solutions of the present disclosure, and form a part of the specification with specific implementations to explain the technical solutions, principle and effect of the present disclosure.

Unless otherwise specified or defined, in different drawings, the same reference numerals represent the same or similar technical features. For the same or similar technical features, different reference numerals may also be used.

For the convenience of description, in the following drawings, FIG. 1 to FIG. 19 mainly illustrate a valve locking device, and FIG. 20 to FIG. 32 mainly illustrate an artificial valve. Some of the drawings illustrate the combination of the valve locking device and the artificial valve.

Figure 1:
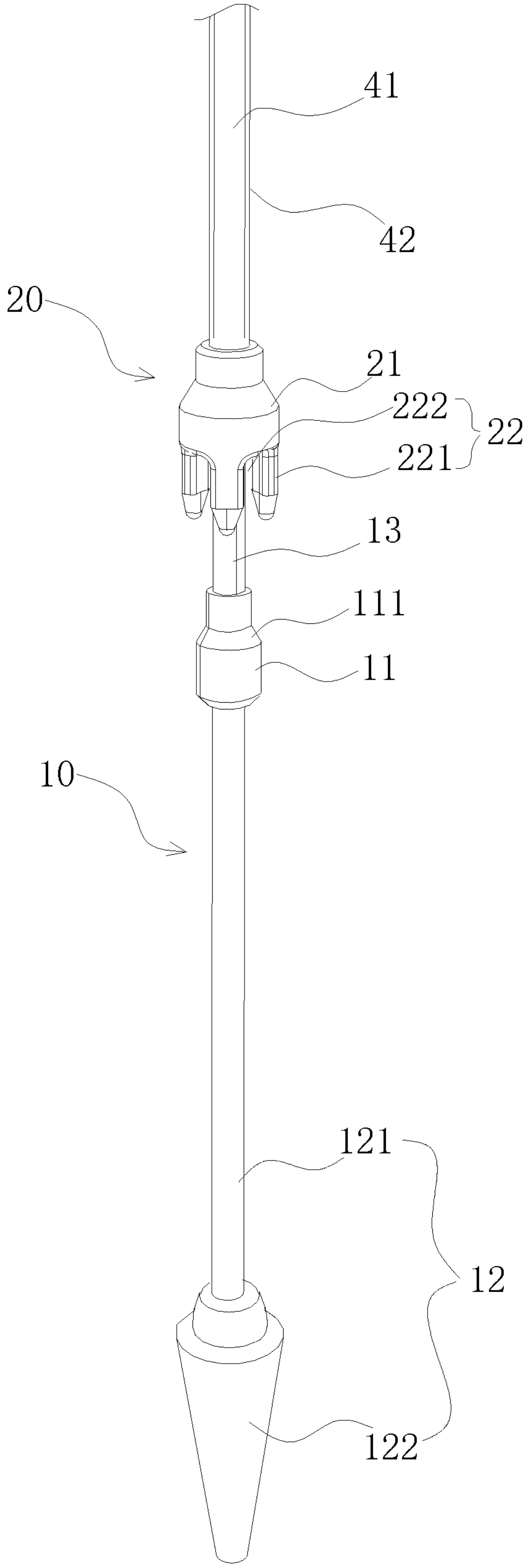
Figure 2:
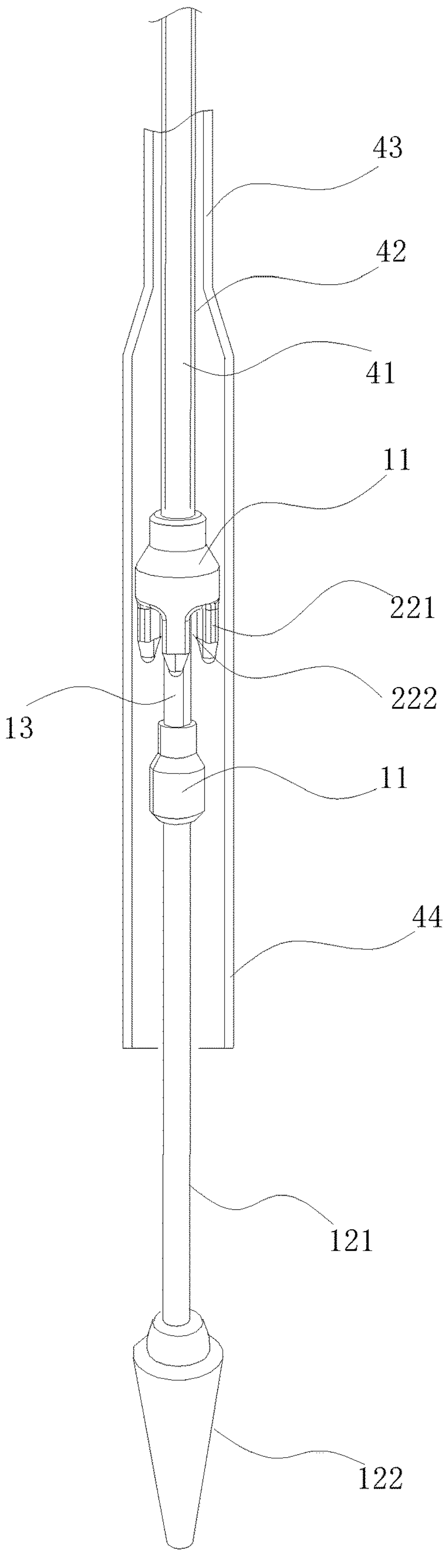
Figure 3:
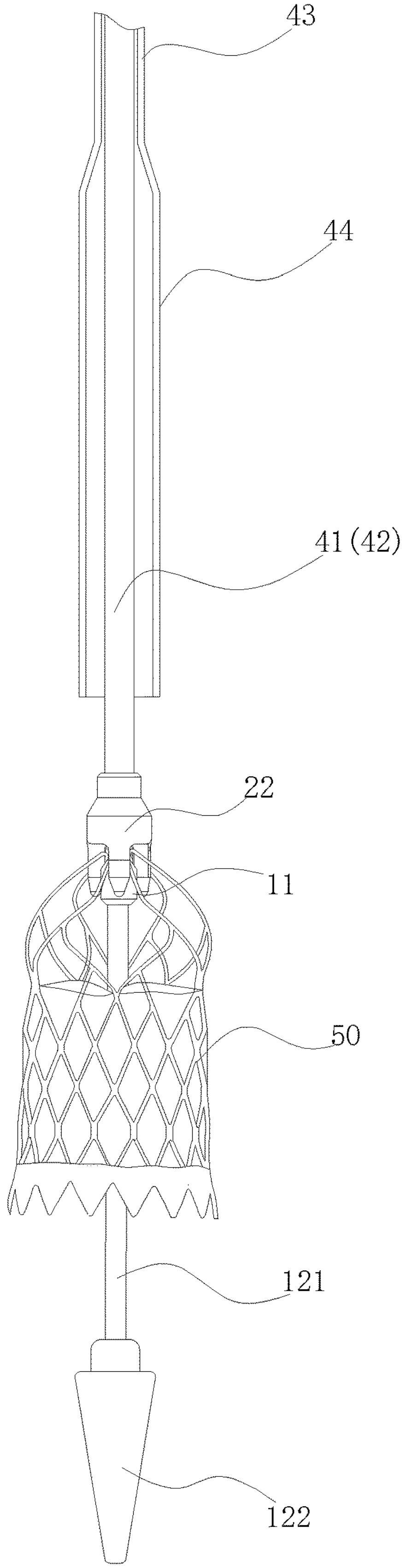
Figure 4:
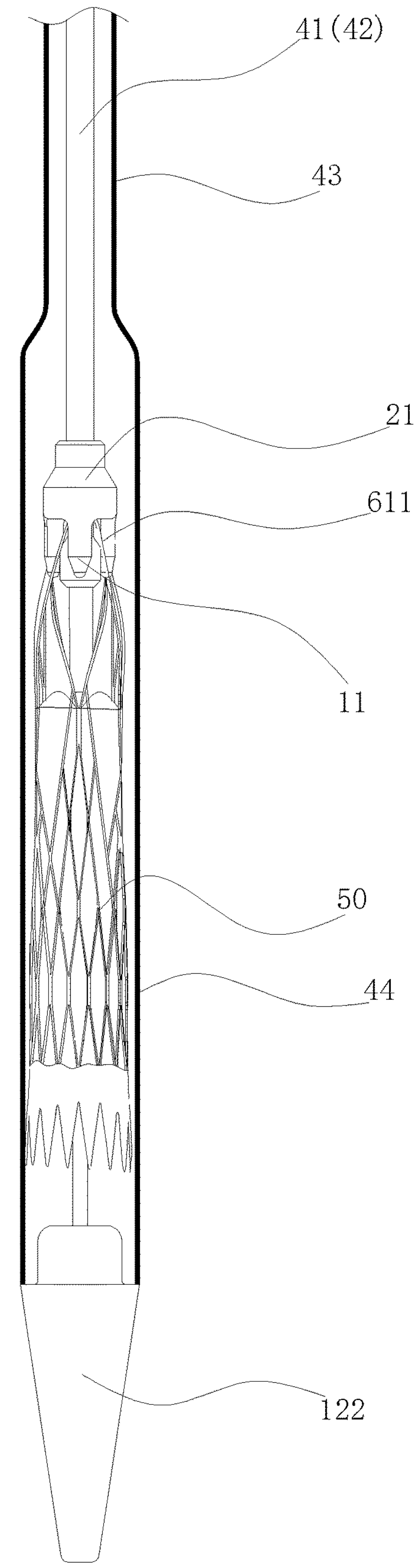
Figure 5:
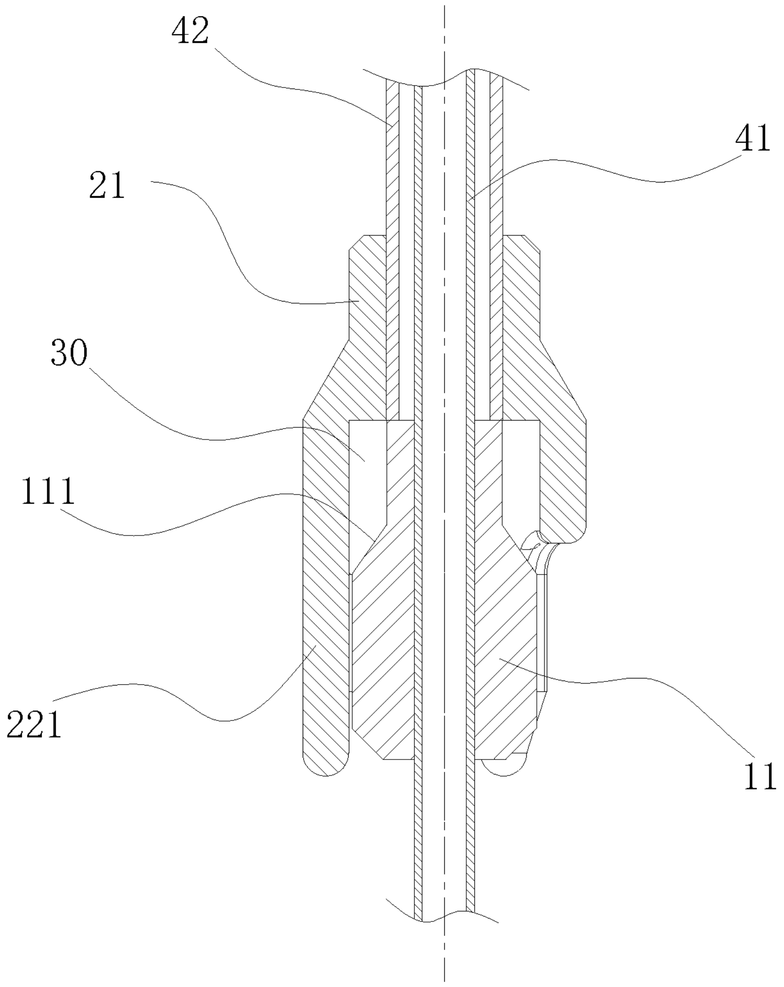
Figure 6:
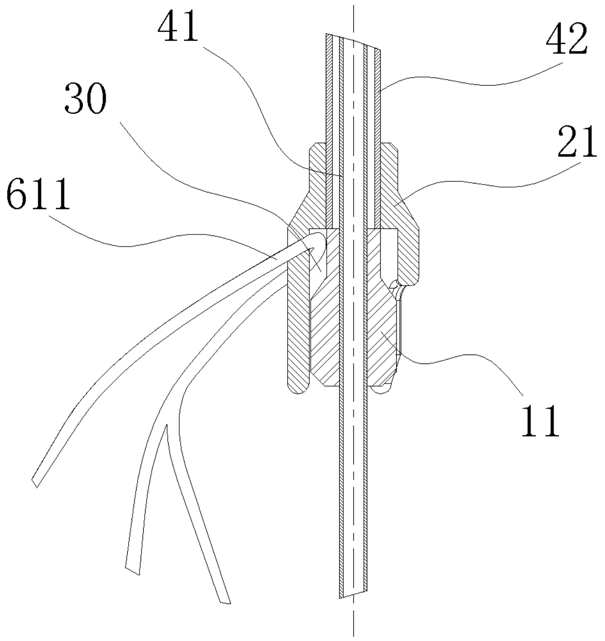
Figure 7:
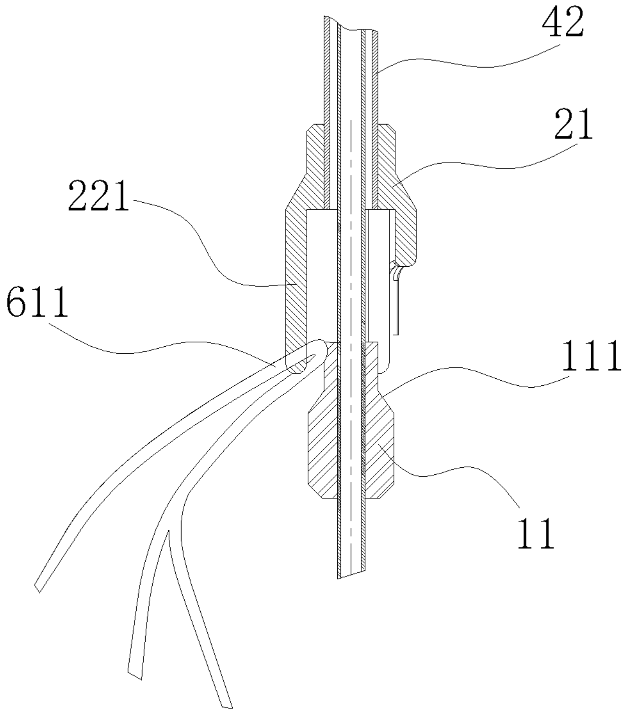
Figure 8:
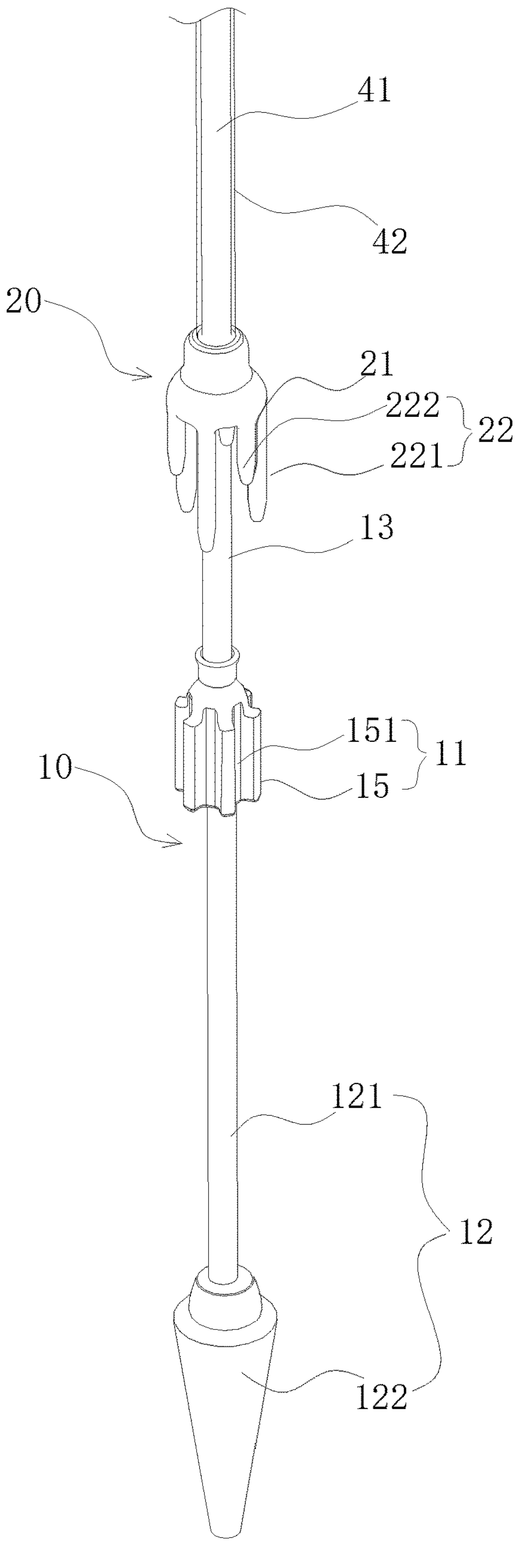
Figure 9:
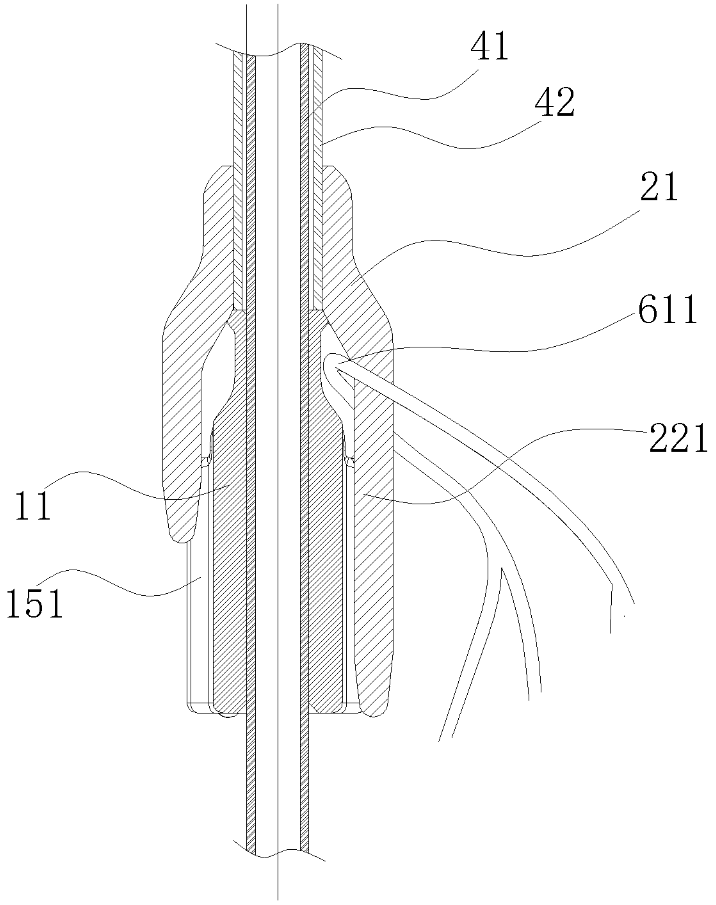
Figure 10:
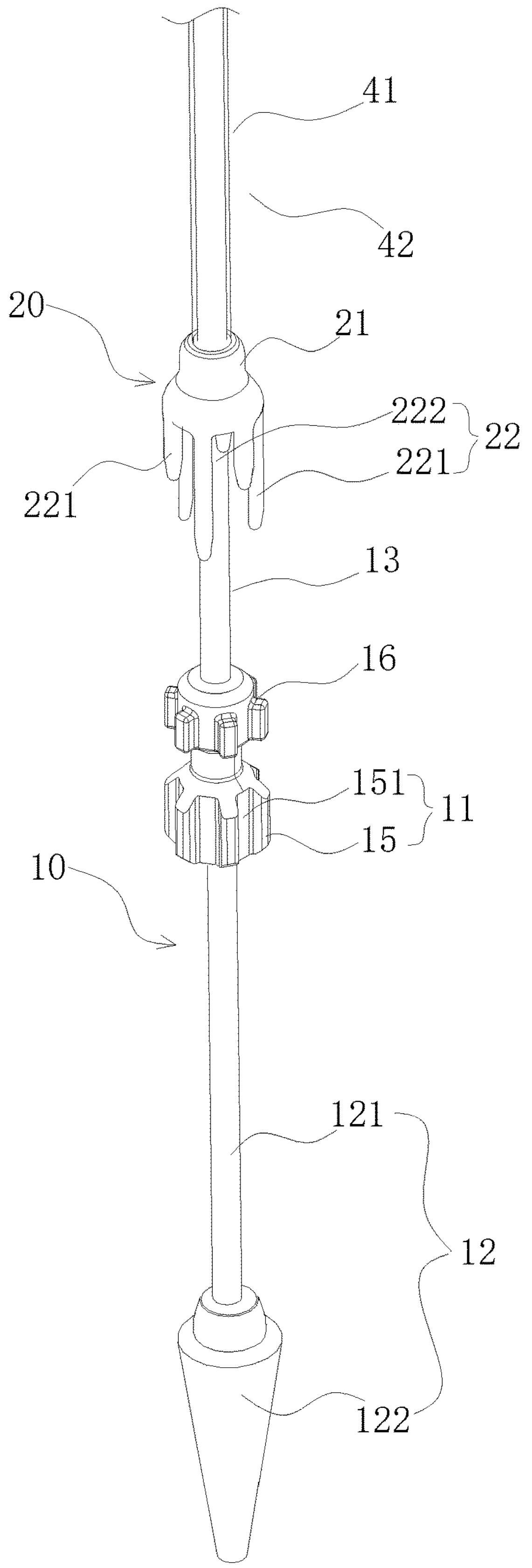
Figure 11:
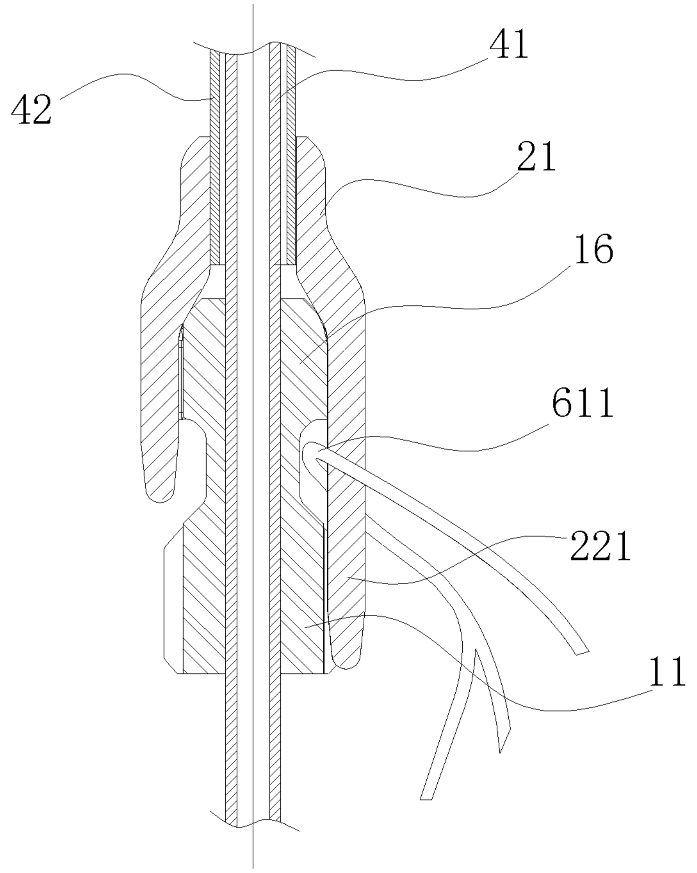
Figure 12:
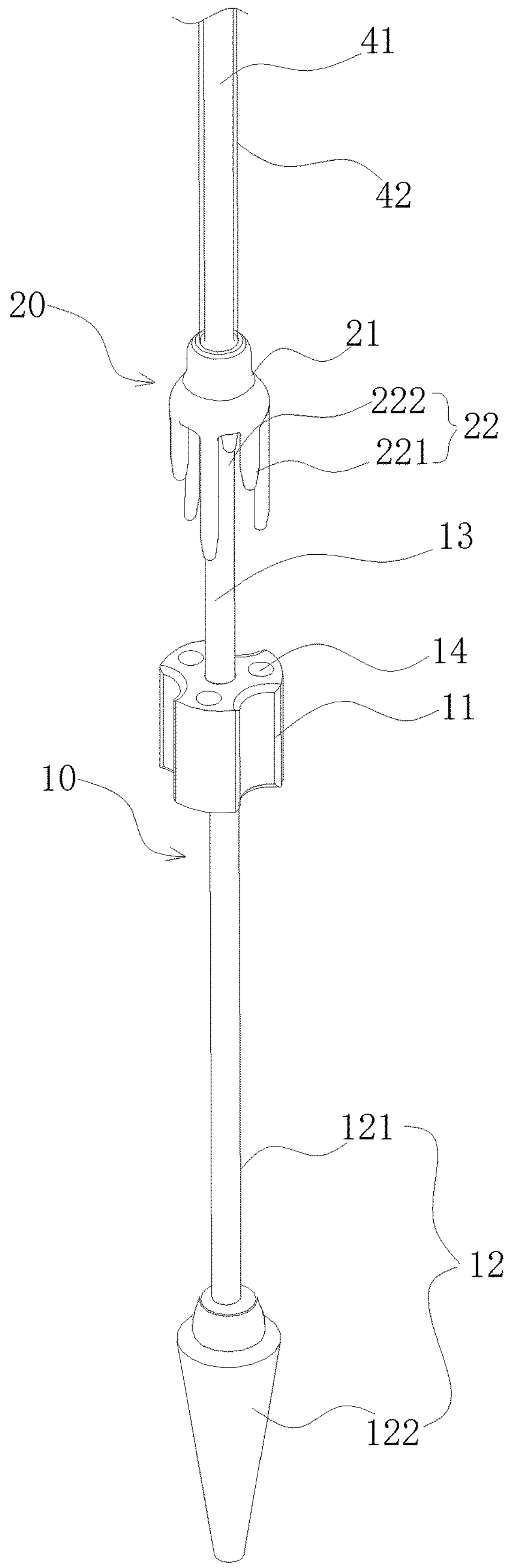
Figure 13:
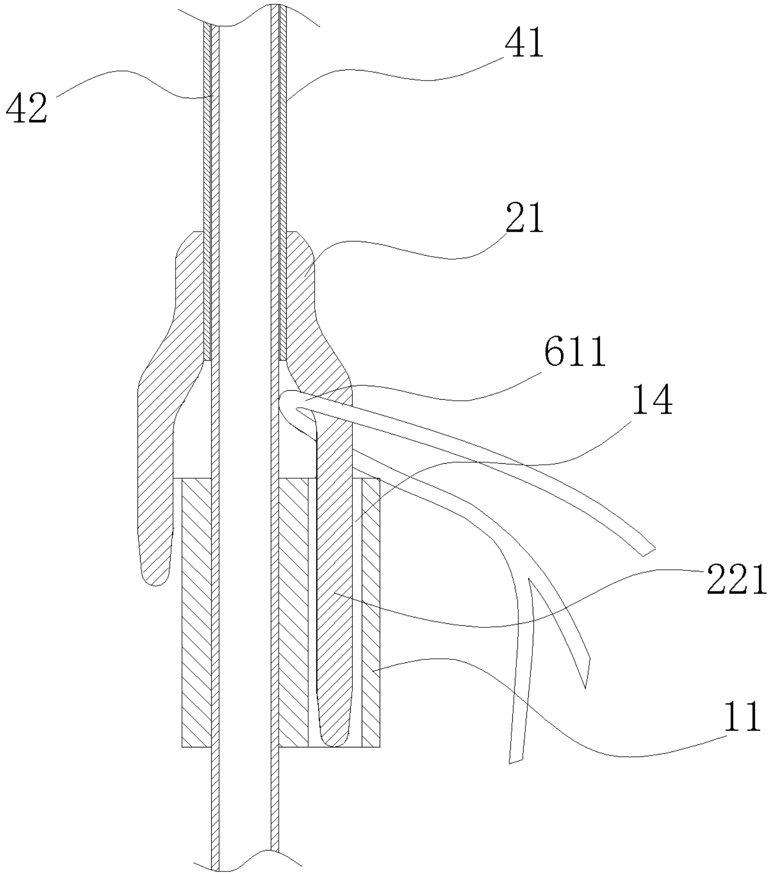
Figure 14:
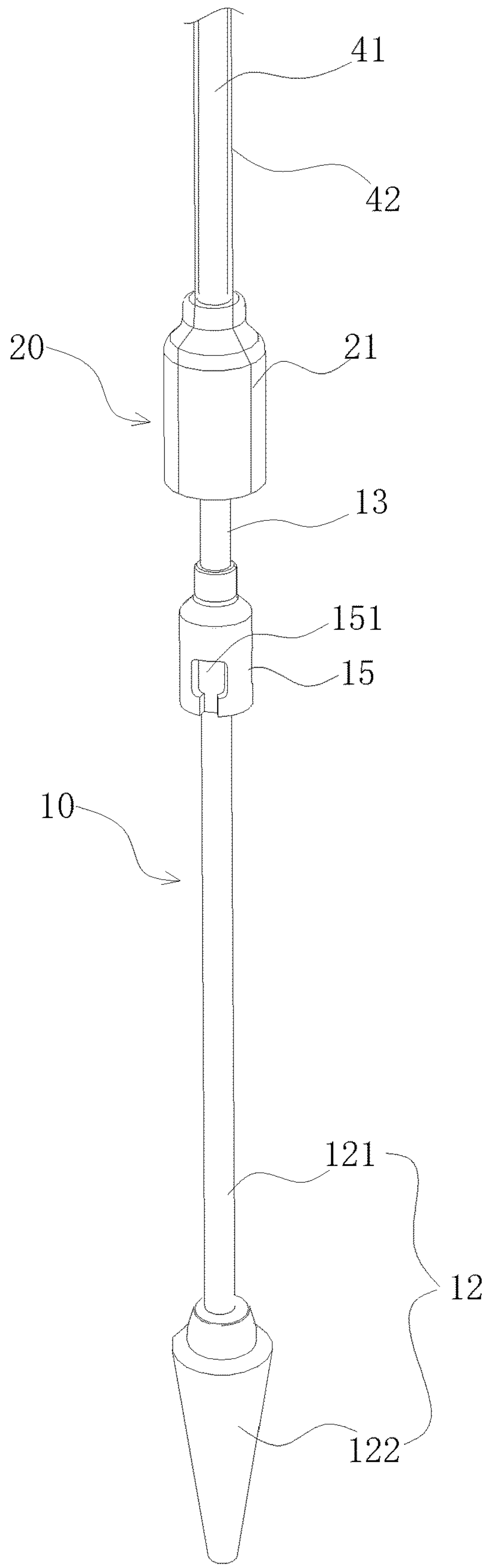
Figure 15:
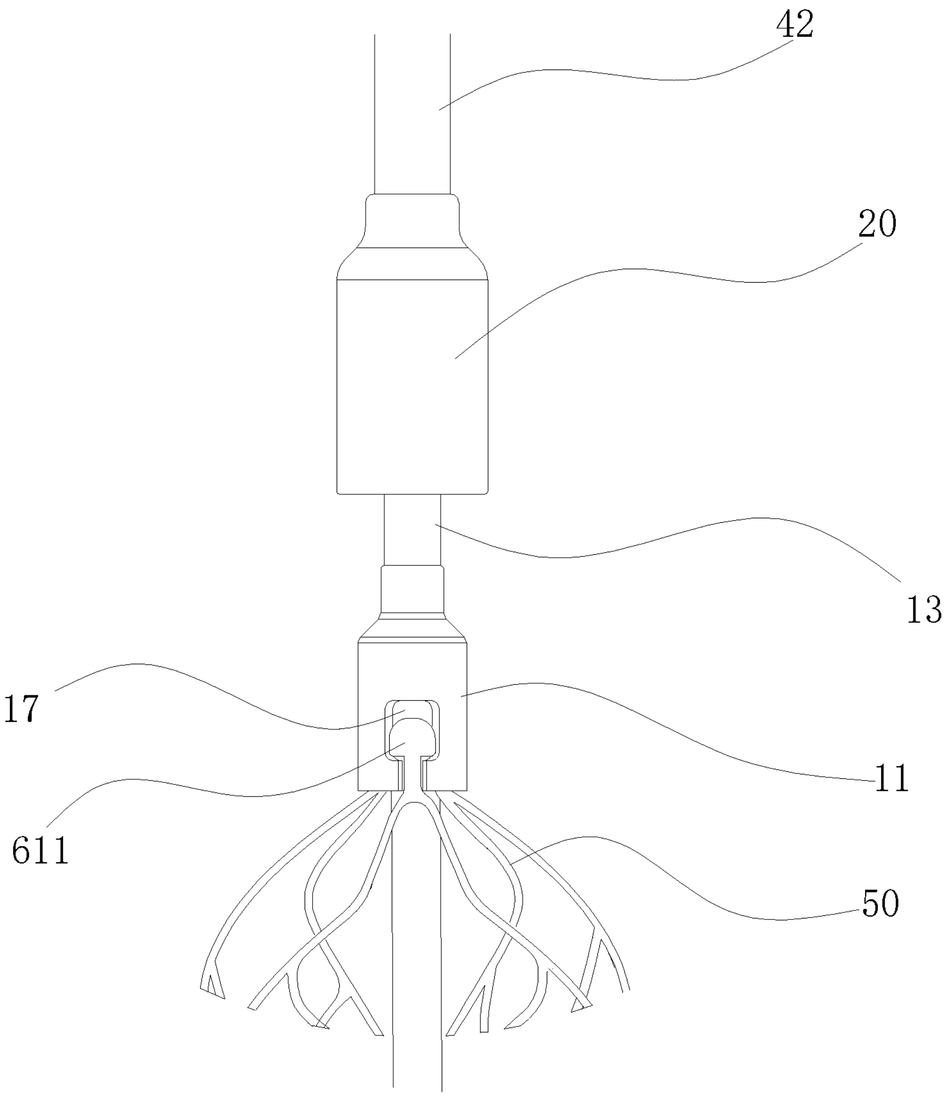
Figure 16:
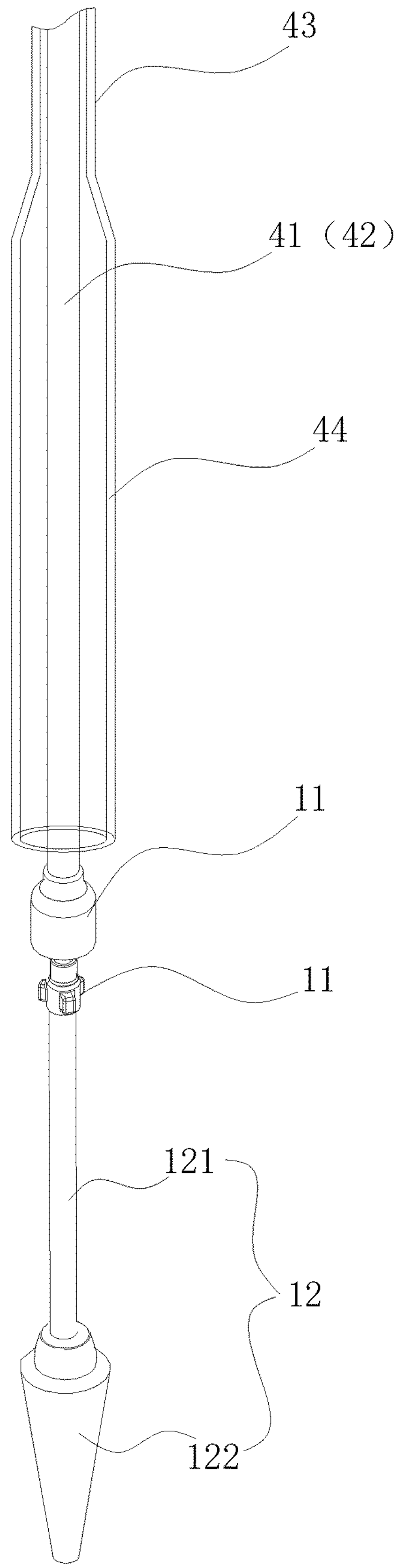
Figure 17:
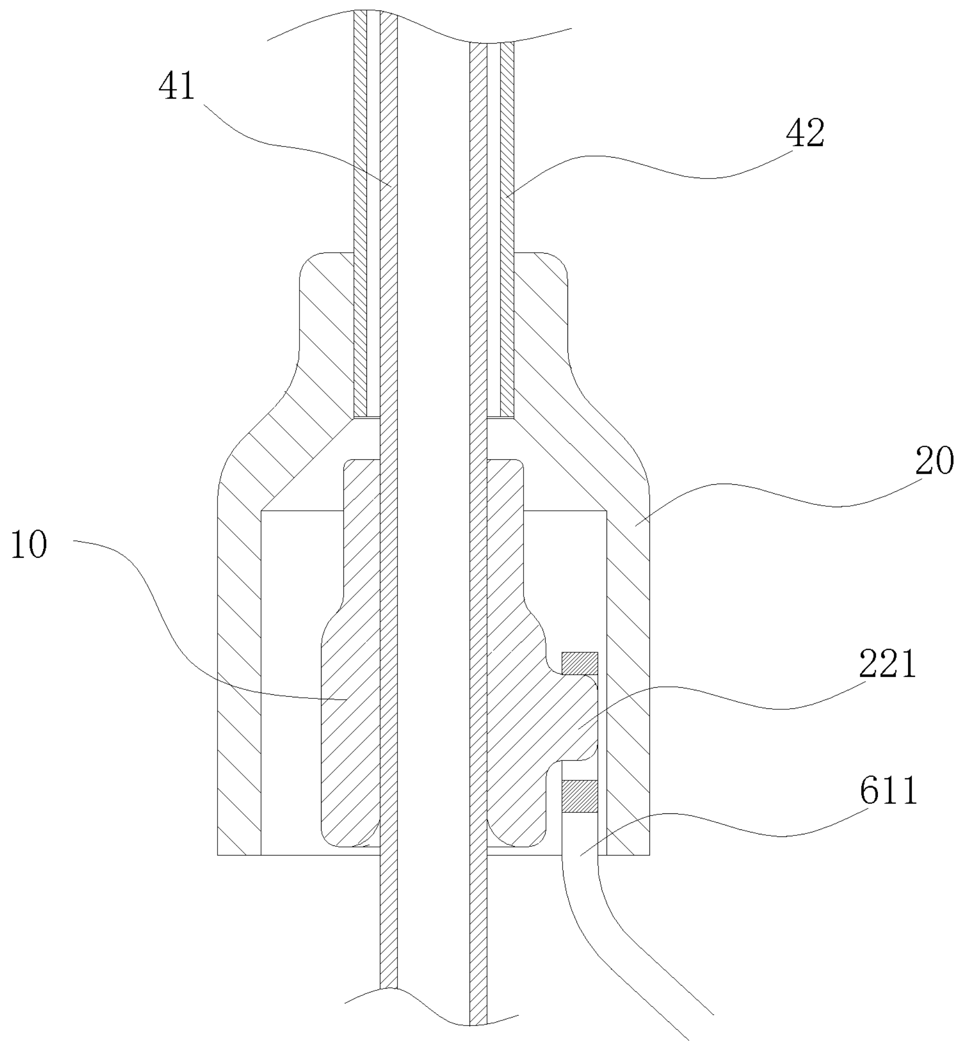
Figure 18:
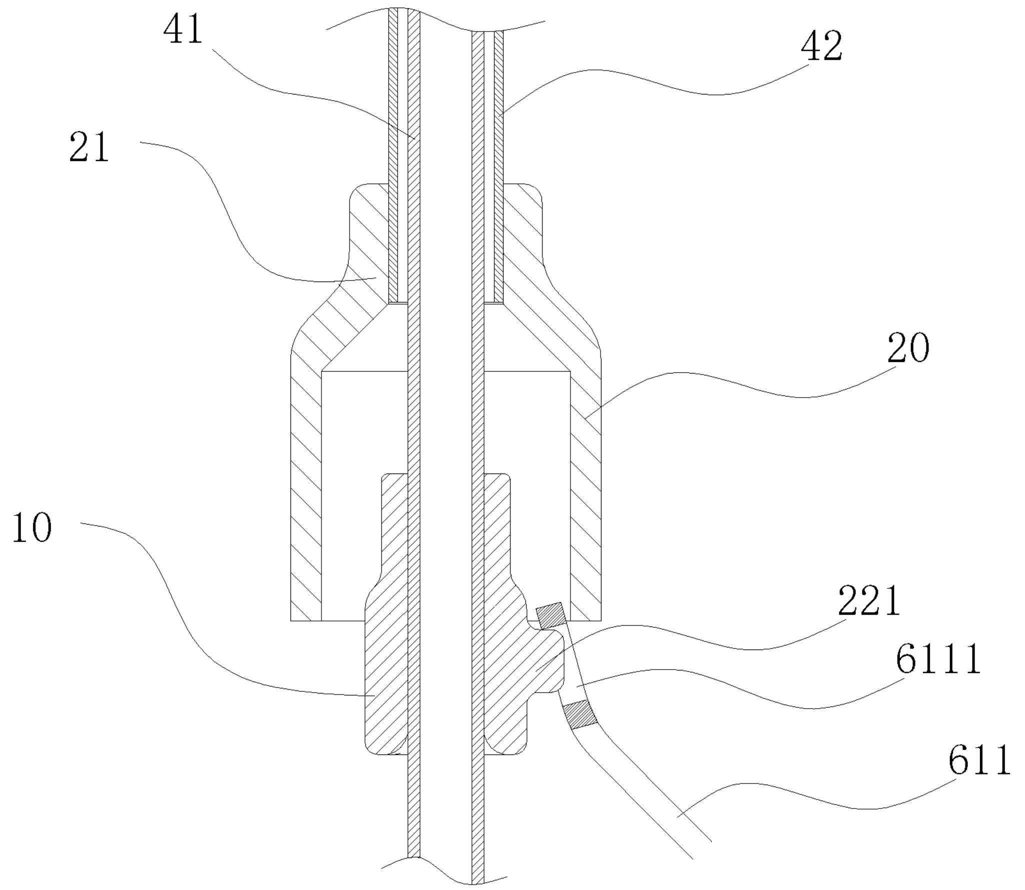
Figure 19:
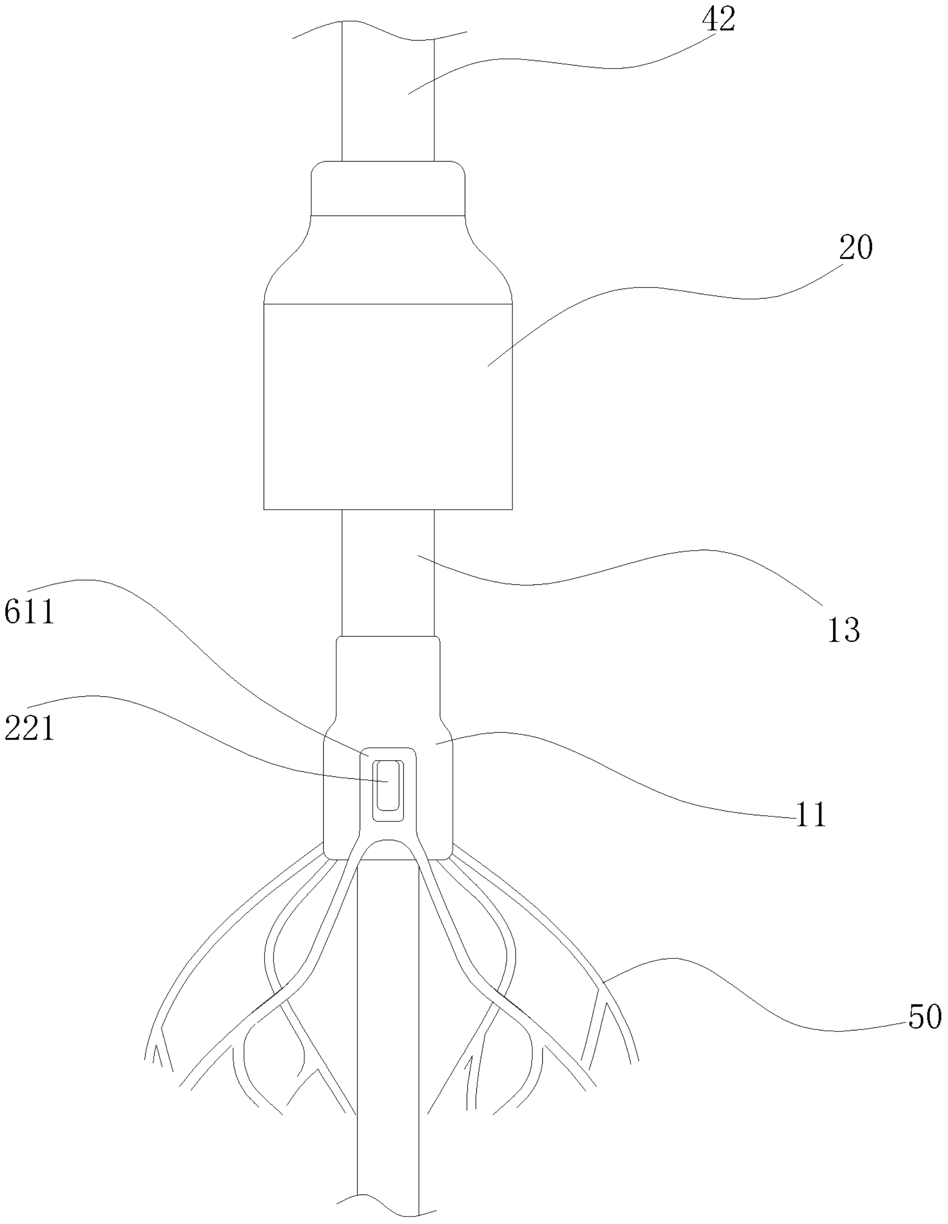
Figure 20:
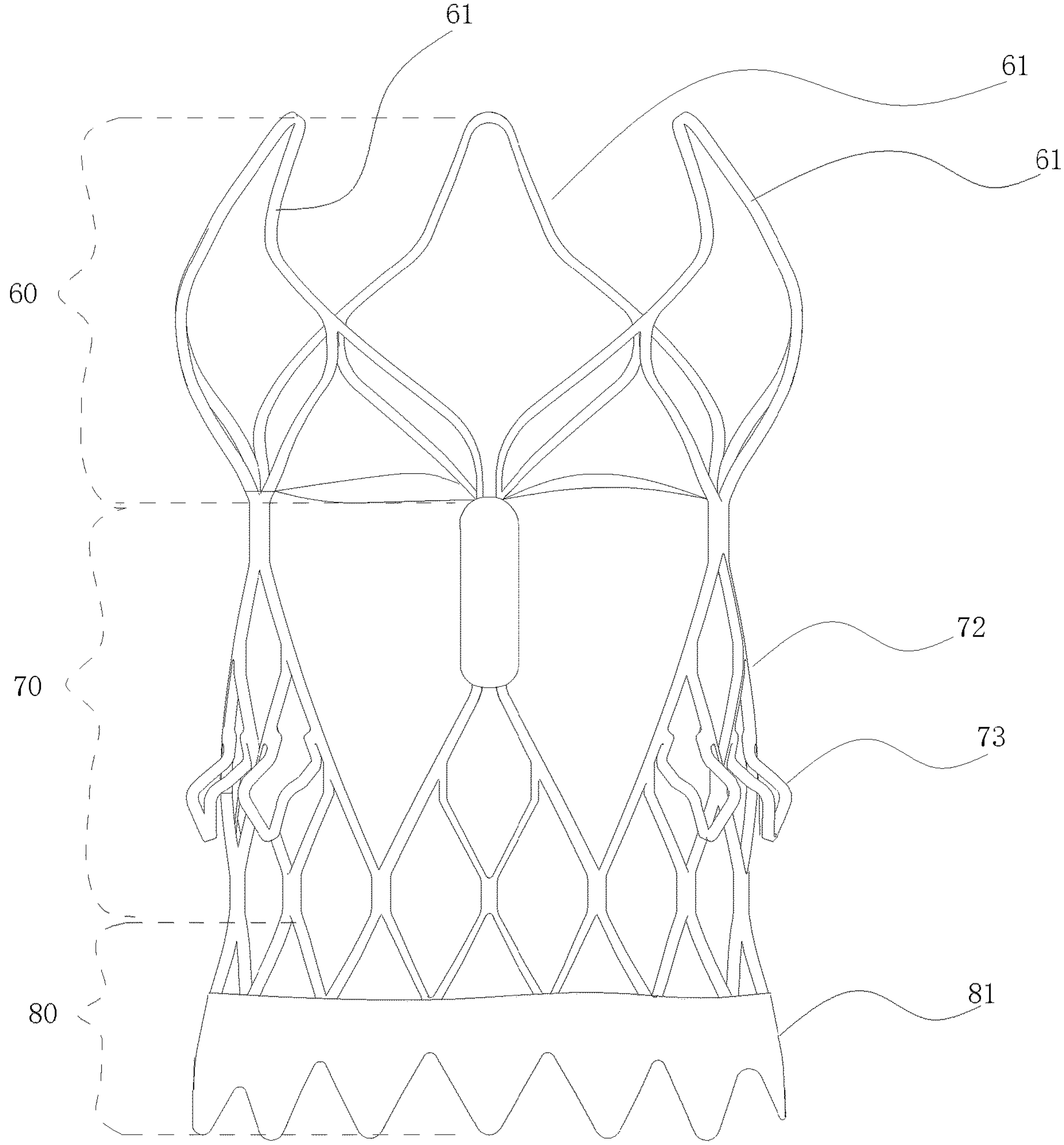
Figure 21:
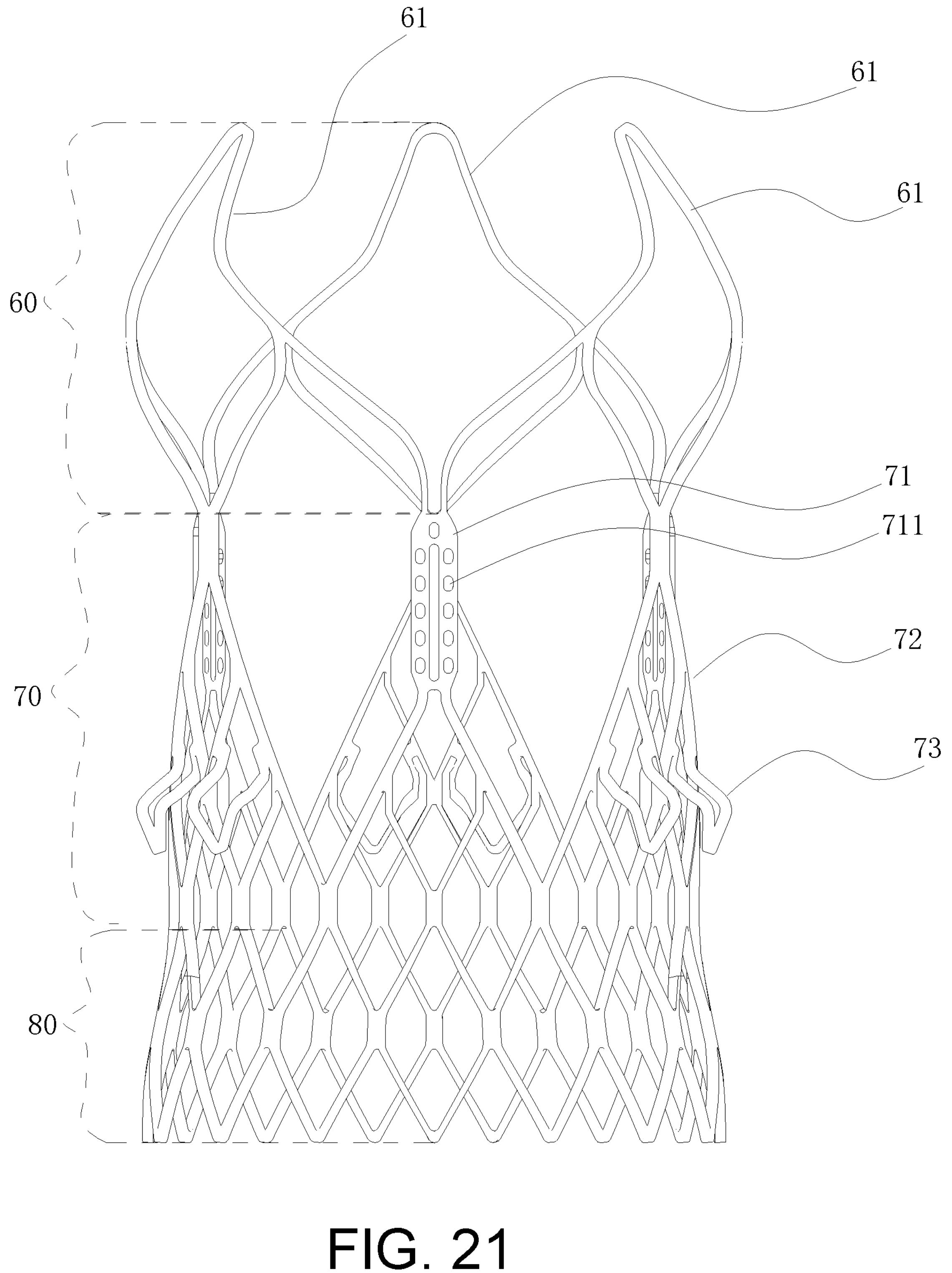
Figure 22:
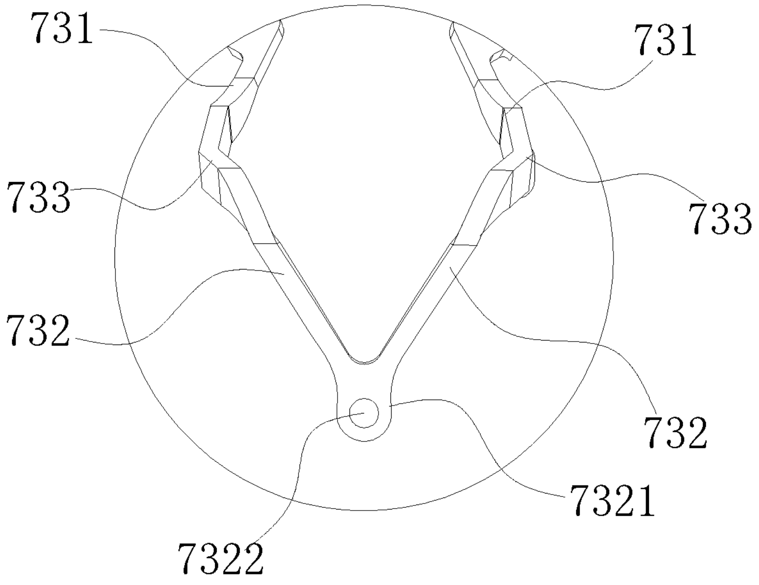
Figure 23:
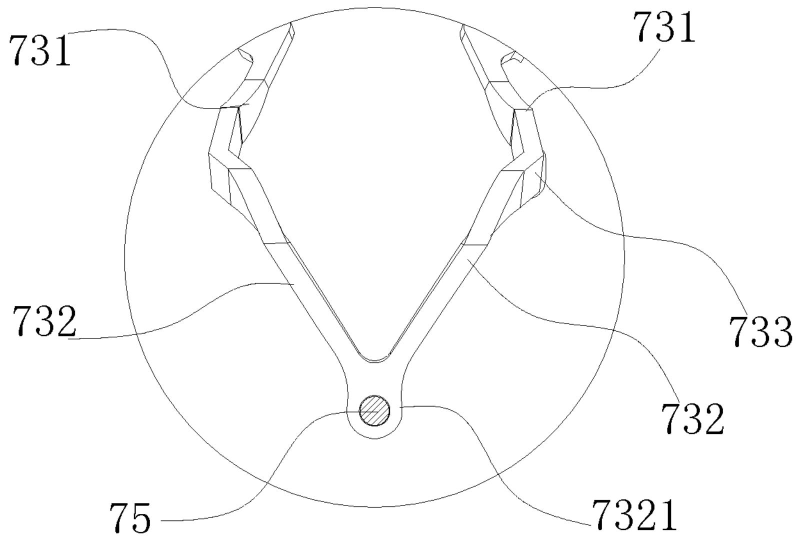
Figure 24:
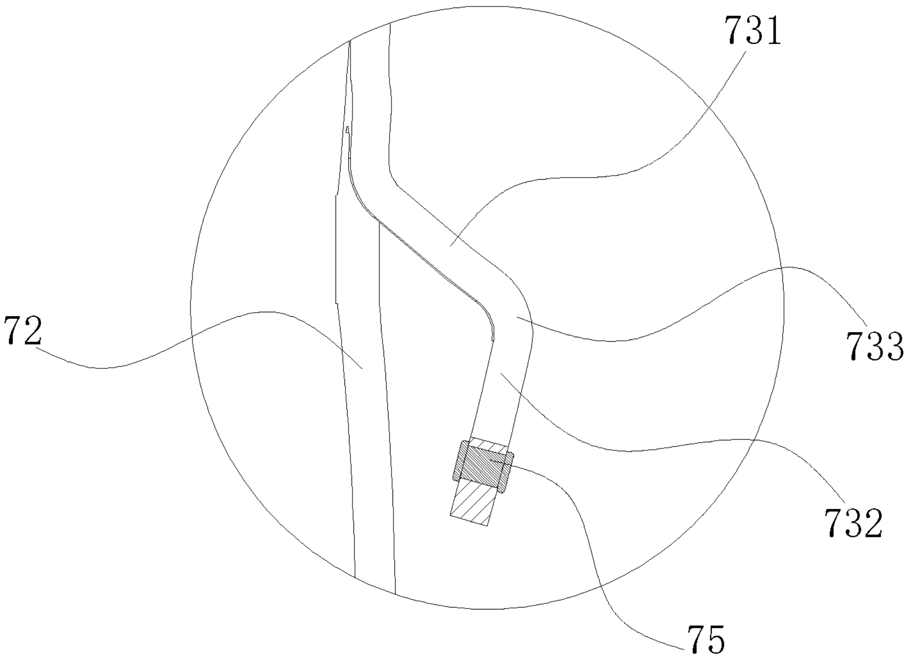
Figure 25:
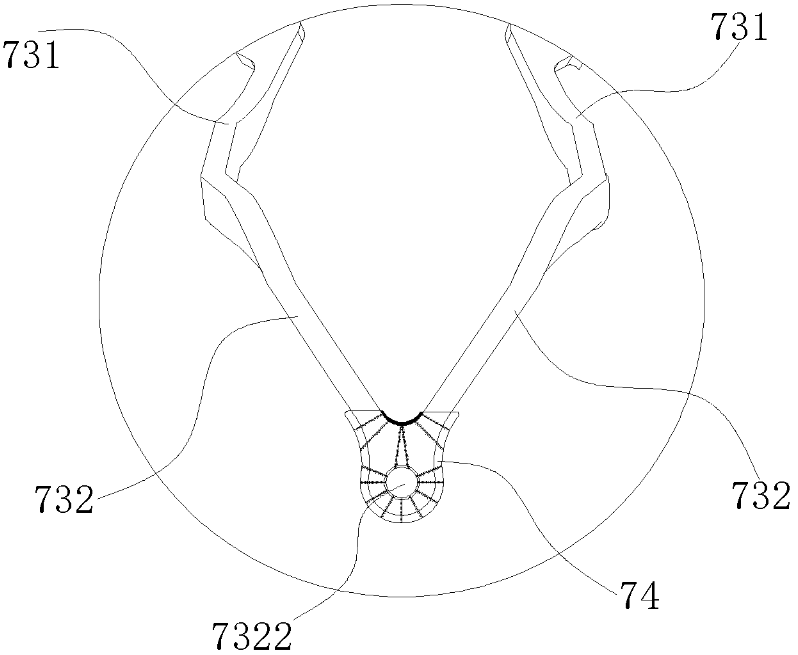
Figure 26:
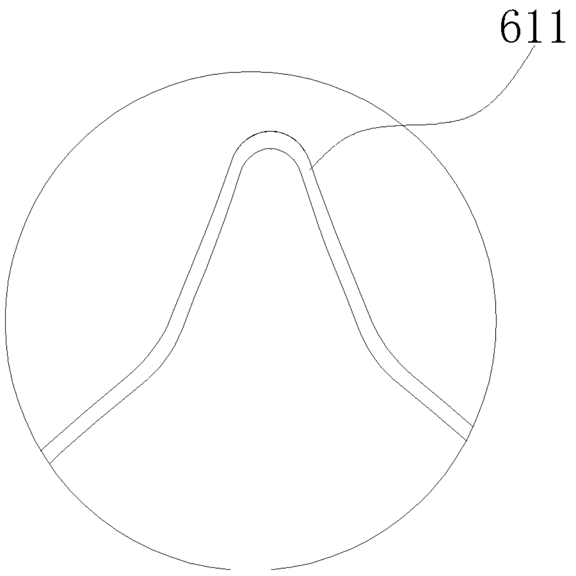
Figure 27:
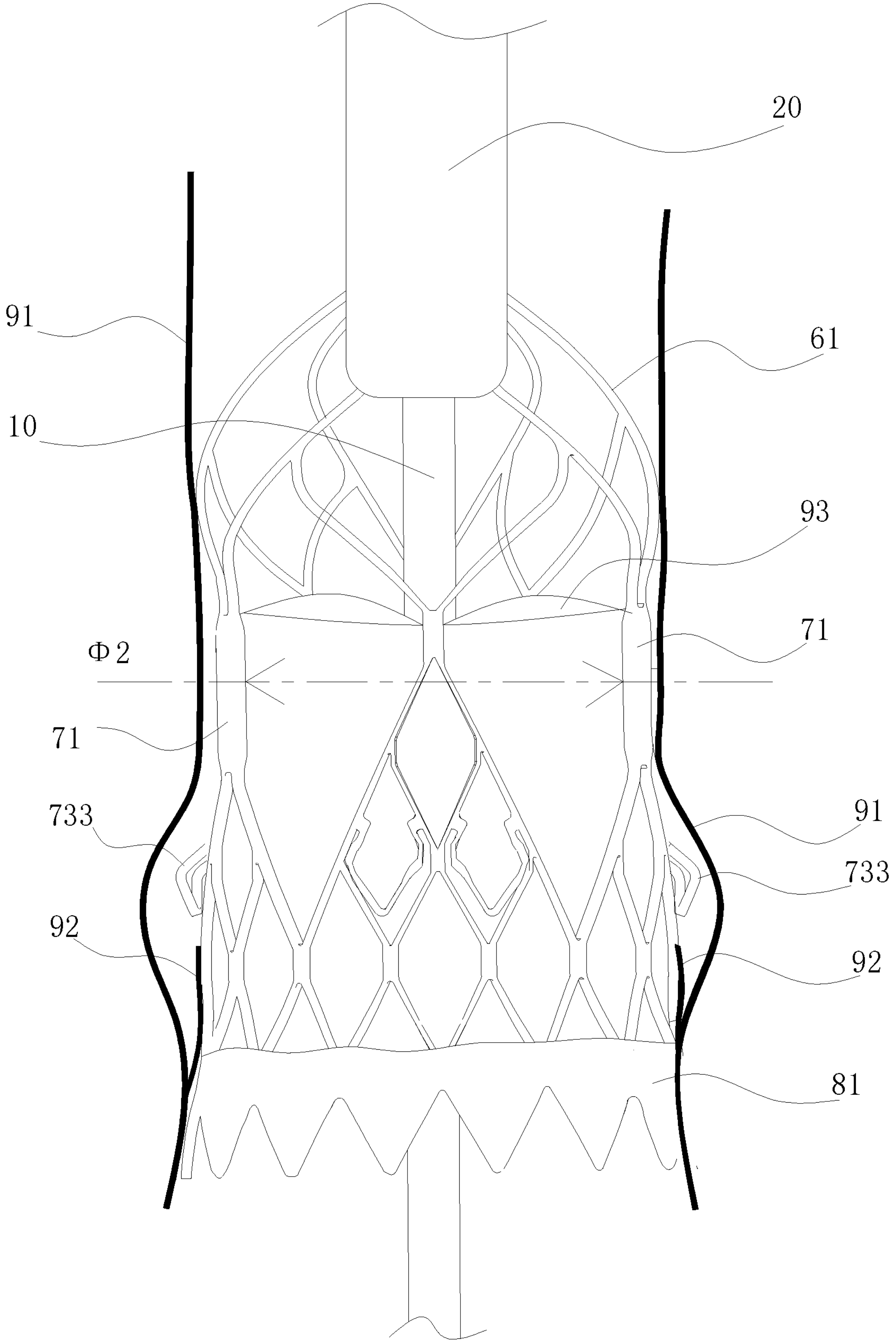
Figure 28:
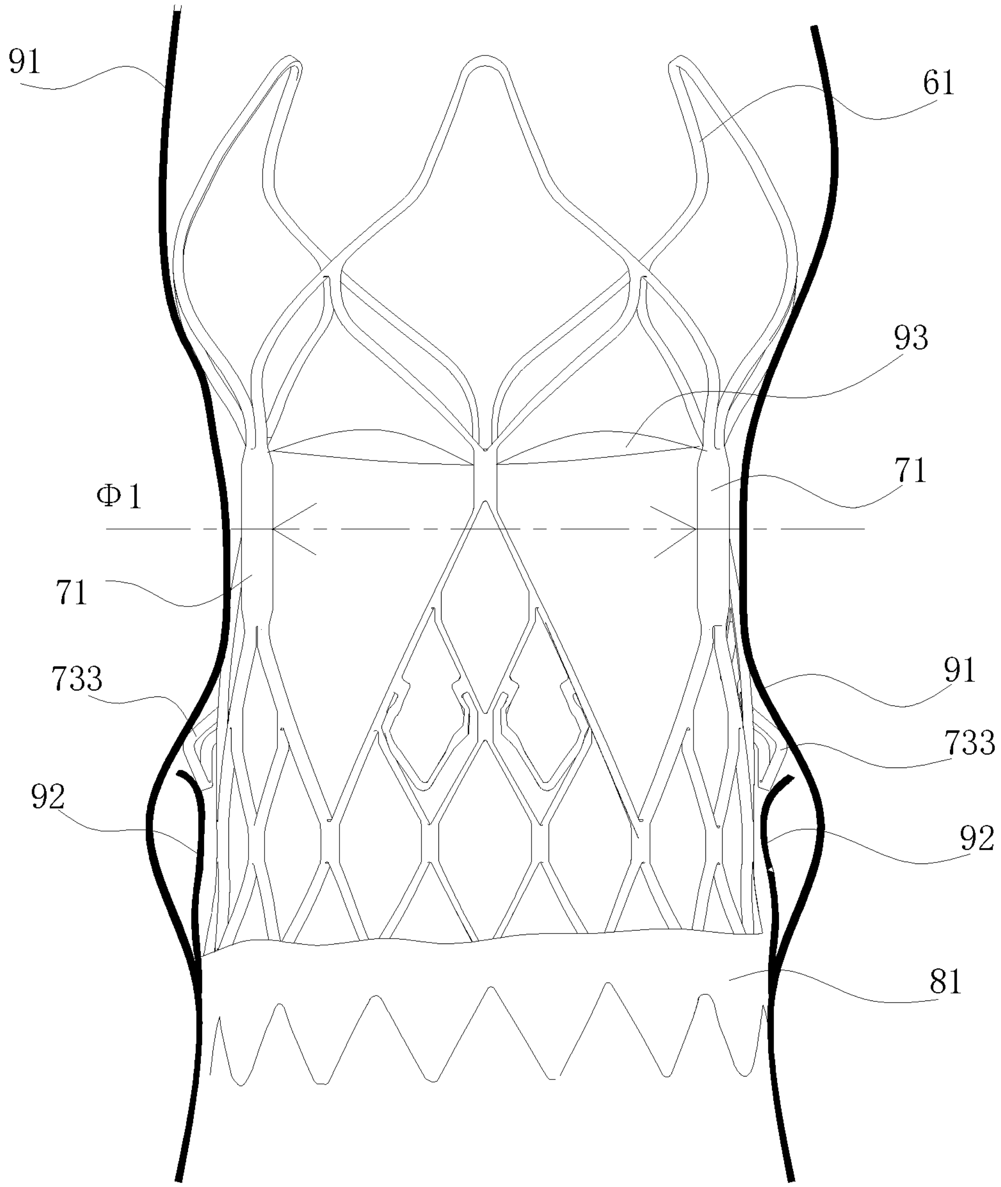
Figure 29:
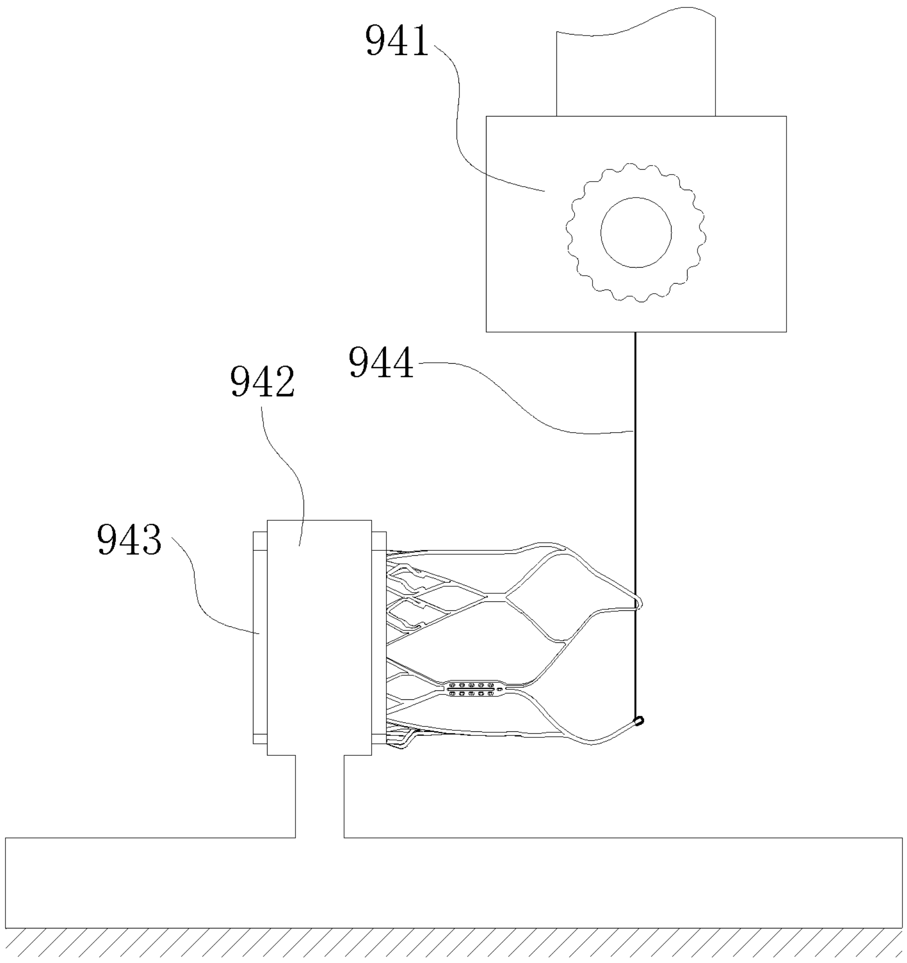
Figure 30:
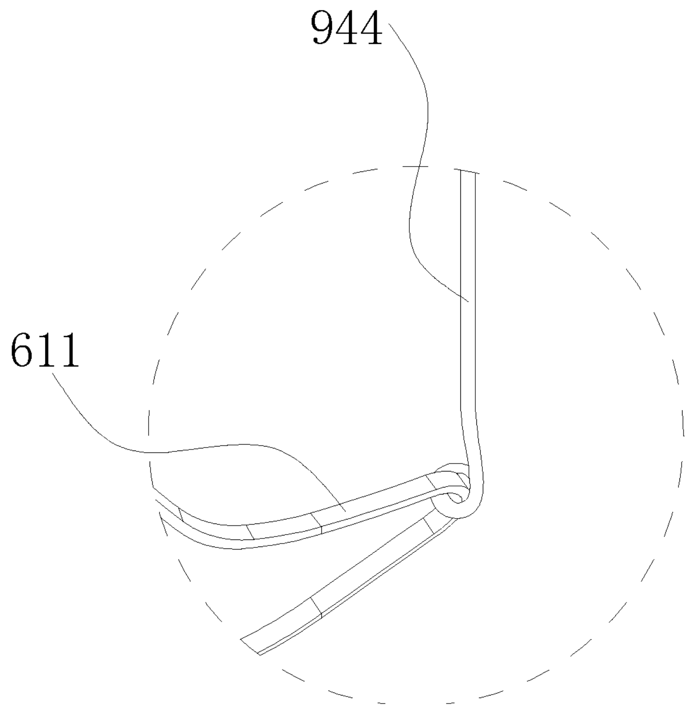
Figure 31:
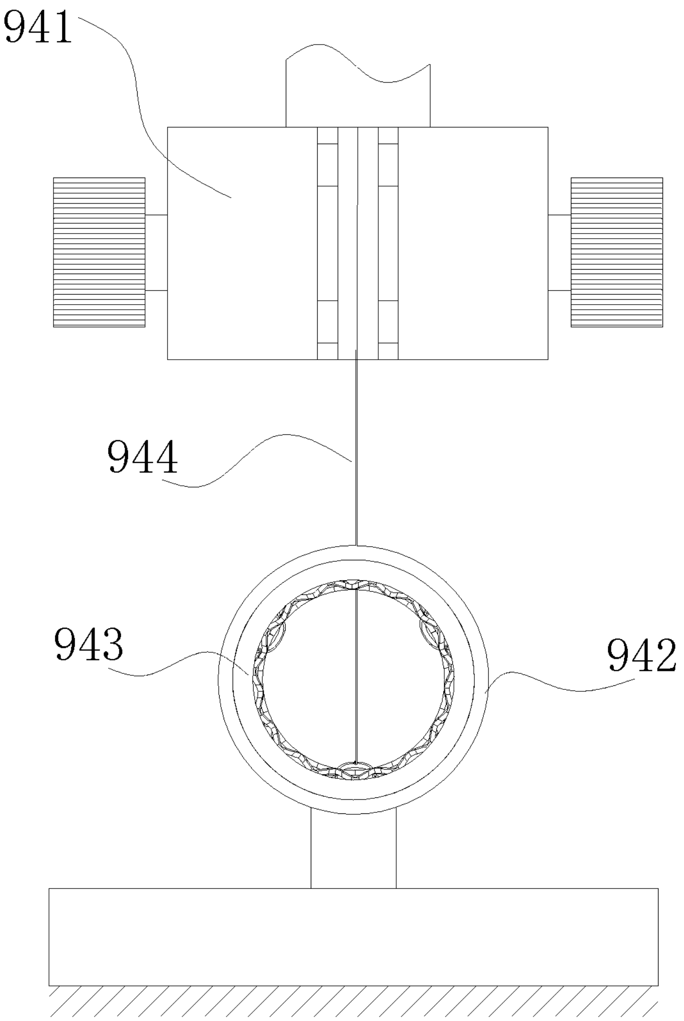
Figure 32:
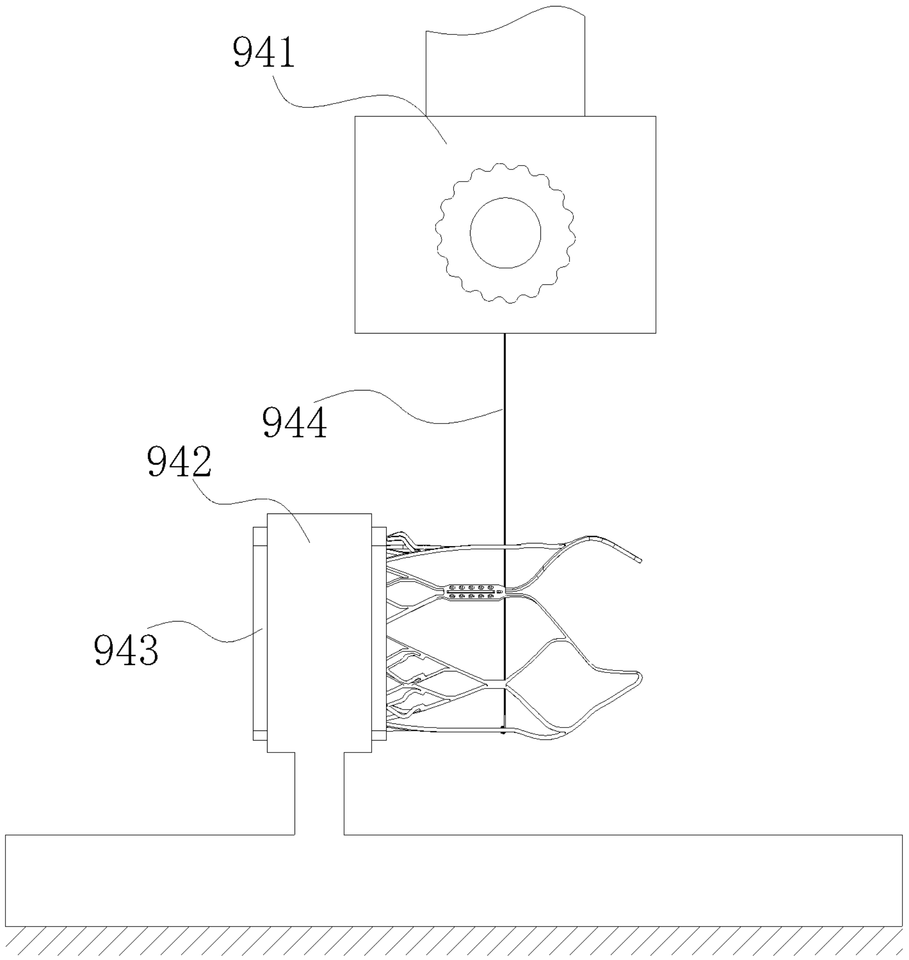
Figure 33:
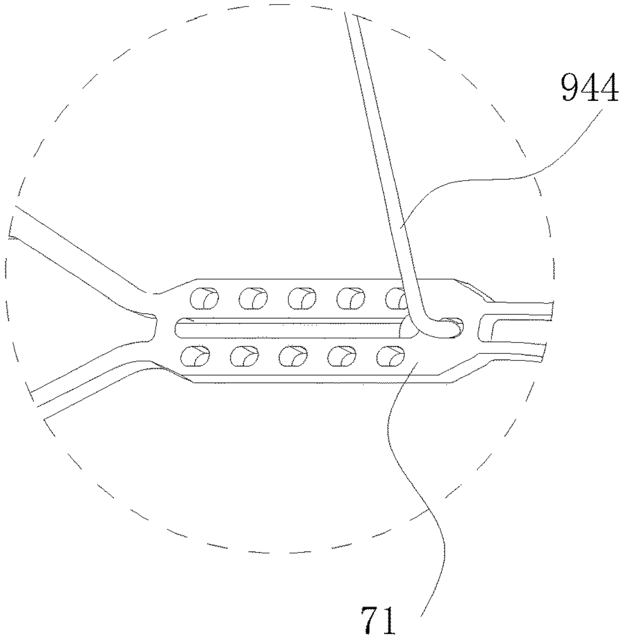
Figure 34:
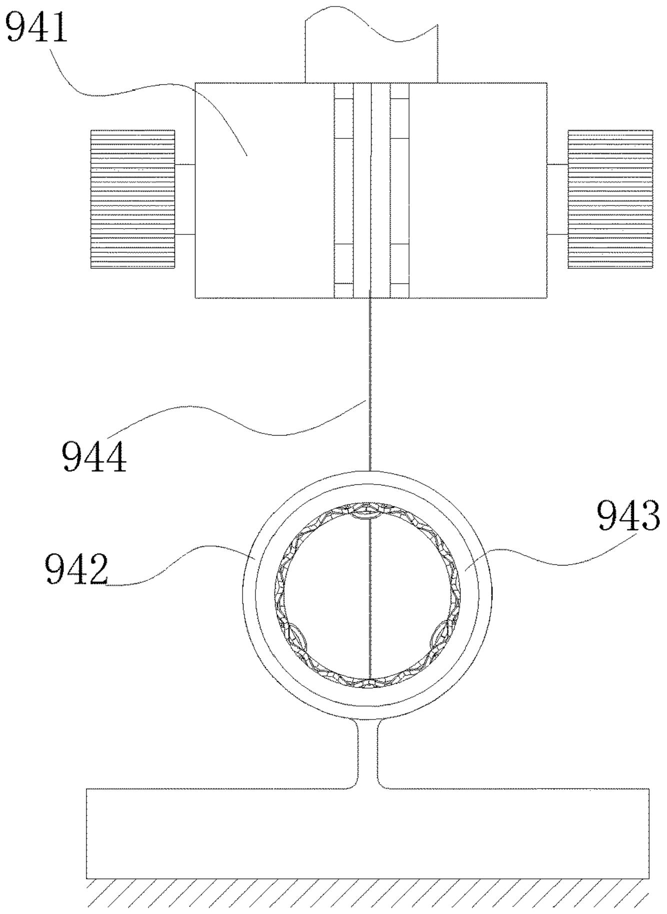
Figure 35:
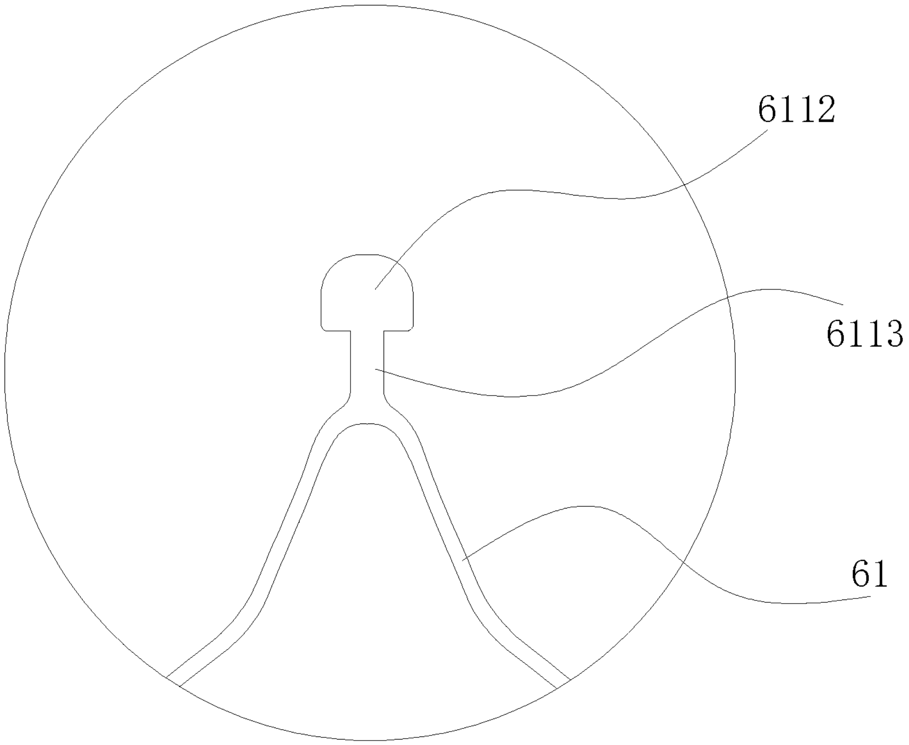
Figure 36:
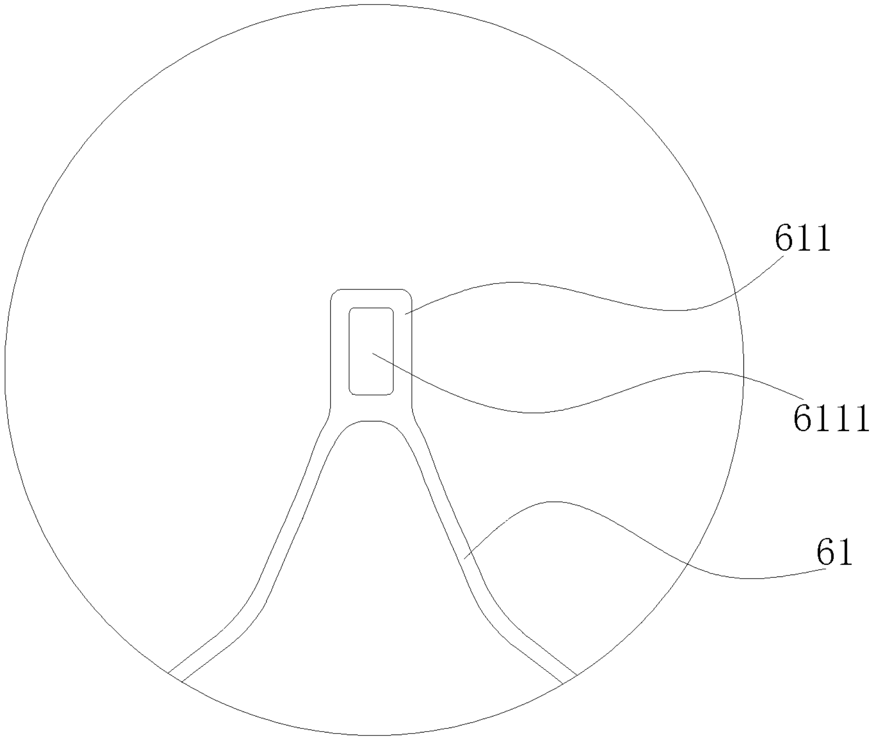

FIG. 1 is a structural diagram of a valve locking device of Embodiment I according to the present disclosure;

FIG. 2 is a structural diagram of a valve delivery device of Embodiment I according to the present disclosure;

FIG. 3 is a structural diagram of the valve delivery device of Embodiment I according to the present disclosure, wherein the valve is in full-height pre-released state but locked;

FIG. 4 is a structural diagram of the valve delivery device of Embodiment I according to the present disclosure, wherein the valve is in complete withdrawal state;

FIG. 5 is a partial sectional view of the valve locking device of Embodiment I according to the present disclosure;

FIG. 6 is a partial schematic diagram of the valve locking device of Embodiment I in locked state according to the present disclosure;

FIG. 7 is a partial schematic diagram of the valve locking device of Embodiment I in unlocked state according to the present disclosure;

FIG. 8 is a structural diagram of a valve locking device of Embodiment II according to the present disclosure;

FIG. 9 is a partial schematic diagram of the valve locking device of Embodiment II in locked state according to the present disclosure;

FIG. 10 is a structural diagram of a valve locking device of Embodiment III according to the present disclosure;

FIG. 11 is a partial schematic diagram of a valve locking device of Embodiment III in locked state according to the present disclosure;

FIG. 12 is a structural diagram of a valve locking device of Embodiment IV according to the present disclosure;

FIG. 13 is a partial schematic diagram of a valve locking device in locked state according to Embodiment IV of the present disclosure;

FIG. 14 is a structural diagram of a valve locking device of Embodiment V according to the present disclosure;

FIG. 15 is a partial schematic diagram of a valve locking device of Embodiment V in unlocked and unreleased state according to the present disclosure;

FIG. 16 is a structural diagram of a valve locking device of Embodiment VI according to the present disclosure;

FIG. 17 is a partial cross-sectional view of a valve locking device of Embodiment VI in locked state according to the present disclosure;

FIG. 18 is a partial sectional view of a valve locking device of Embodiment VI in unlocked state according to the present disclosure;

FIG. 19 is a partial schematic diagram of a valve locking device of Embodiment VI in unlocked state according to the present disclosure;

FIG. 20 is a structural diagram of an artificial valve of Embodiment VII according to the present disclosure;

FIG. 21 is a structural diagram of a stent of the artificial valve of Embodiment VII according to the present disclosure;

FIG. 22 is a partially enlarged view of an anchoring frame;

FIG. 23 is a structural diagram of an anchoring frame provided with a developing positioning piece;

FIG. 24 is a side view of the structure shown in FIG. 23;

FIG. 25 is a structural diagram of an anchoring frame provided with a protective sleeve;

FIG. 26 is a partially enlarged view of a locking end of the artificial valve of Embodiment VII of the present disclosure;

FIG. 27 is a side view of an artificial valve of Embodiment VII in locked (full-height pre-released) state according to the present disclosure;

FIG. 28 is a side view of an artificial valve of Embodiment VII in unlocked (fully released) state according to the present disclosure;

FIG. 29 is a first direction view of the structural stiffness test of a locking end in Embodiment VII;

FIG. 30 is a partially enlarged view of FIG. 29;

FIG. 31 is a second direction view of the structural stiffness test of the locking end in Embodiment VII;

FIG. 32 is a first direction view of the structural stiffness test of a suture rod in Embodiment VII;

FIG. 33 is a partially enlarged view of FIG. 22;

FIG. 34 is a second direction view of the structural stiffness test of the suture rod in Embodiment VII;

FIG. 35 is a partially enlarged view of a locking end of the artificial valve of Embodiment VIII of the present disclosure; and FIG. 36 is a partially enlarged view of a locking end of an artificial valve of Embodiment IX according to the present disclosure.

DETAILED DESCRIPTION OF THE EMBODIMENTS

In order to facilitate the understanding of the present disclosure, specific embodiments of the present disclosure will be described in more detail as below with reference to the drawings of the specification.

Unless otherwise specified or defined, all technical and scientific terms used herein have the same meanings as those commonly understood by those skilled in the art. In combination with the realistic scenarios of the technical solutions of the present disclosure, all the technical and scientific terms used herein can also have meanings corresponding to the purposes of realizing the technical solutions of the present disclosure.

Unless otherwise specified or defined, the terms "first, second . . . " used herein are only used to distinguish names and does not represent specific quantities or orders.

Unless otherwise specified or defined, the term "and/or" used herein includes any and all combinations of one or more related listed items.

It should be noted that when one element is considered to be "fixed" to the other element, it may be directly fixed on the other element, or via an intermediate element. When one element is considered to be "connected" to the other element, it may be directly connected to the other element, or via an intermediate element at the same time. When one element is considered to be "mounted" on the other element, it can be directly mounted on the other element, or via an intermediate element at the same time. When one element is considered to be "arranged" on the other element, it may be directly arranged on the other element, or via an intermediate element at the same time.

Unless otherwise specified or defined, "said" and "this" used herein refer to the technical features or technical contents previously mentioned or described at the corresponding locations. The technical features or technical contents may be the same or similar to those mentioned.

There is no doubt that the technical contents or technical features that are contrary to or obviously contradicted to the purpose of the present disclosure should be excluded.

Embodiment I

As shown in FIG. 1 to FIG. 7, a valve delivery device includes a sheath 44, a third actuator 43 and a valve locking device.

The valve locking device, as shown in FIG. 1 and FIG. 5, includes a first locking member 10 and a second locking member 20. The first locking member 10 and the second locking member 20 are relatively movable. The first locking member 10 is provided with a first locking portion. The second locking member 20 is provided with a second locking portion. A locking position 30 is formed between the first locking portion and the second locking portion. The rear end of the first locking member 10 is connected to a first actuator 41. The rear end of the second locking member 20 is connected to a second actuator 42. The second actuator 42 is in the shape of a hollow tube. The first actuator 41 is sleeved into the hollow portion of the second actuator 42. The first actuator 41 and the second actuator 42 are operated to control the axial movements of the first locking member 10 and the second locking member 20. When the first locking member 10 and the second locking member 20 move relatively, the locking position 30 is in unlocked or locked state.

The second locking member 20 is ring-shaped, which includes a ring body 21 and a clamping body 22. The clamping body 22 is fixedly connected with the ring body 21 and matches a locking seat 11, and the locking position 30 is formed between the clamping body 22 and the locking seat 11. The middle part of ring body 21 is provided with a central hole.

The first locking member 10 includes a locking seat 11, a guiding rod 12 and a matching rod 13. The guiding rod 12 is connected to the front end of the locking seat 11, and the matching rod 13 is connected to the rear end of the locking seat 11. The guiding rod 12 includes a rod body 121 and a guiding head 122. The diameter of the rod body 121 is smaller than that of the locking seat 11 and that of the guiding head 122. The front end of the guiding head 122 is provided with a guiding slope.

Specifically, the clamping body 22 is provided with three finger-shaped clamping protrusions 221, facing toward the front end. A clamping seam 222 is formed between the clamping protrusions 221. Locking ends 611 of the artificial valve 50 are locked within the clamping seam 222. A locking slope 111 is arranged on the locking seat 11. A locking position 30 is formed between the locking slope 111 and the clamping protrusions 221. The second locking member 20 is sleeved on the matching rod 13 of the first locking member 10 through the central hole, and can move axially relative to the matching rod 13 to unlock or lock the locking position 30.

The valve delivery device is as shown in FIG. 2. The third actuator 43 is connected to the rear end of the sheath 44. The sheath 44 and the third actuator 43 are both hollow tubular. The second actuator 42 is sleeved into the hollow portion of the third actuator 43. The inner diameter of the sheath 44 is larger than the radial dimension of the second locking member 20.

Referring to FIG. 3, FIG. 4, FIG. 6 and FIG. 7, the first locking member 10 and the second locking member 20 of the valve locking device can move relatively. By adjusting the positions of the first locking member 10 and the second locking member 20, the locking position 30 can be unlocked (as shown in FIG. 7) or locked (as shown in FIG. 6). During implantation, the locking ends 611 of the artificial valve 50 are locked within the locking position 30 to be locked. The artificial valve can be placed into the sheath by controlling the movement of the sheath, as shown in FIG. 4. After the artificial valve 50 is pushed to the root of patient's aorta, the artificial valve 50 can be pre-released at full-height (as shown in FIG. 3). However, the locking position 30 does not need to be unlocked at this moment. Doctors can pre-evaluate the artificial valve 50, including the operation state of the artificial valve 50, the release position of the artificial valve 50 and the like. If the artificial valve 50 meets the requirements via evaluation, the locking position 30 is unlocked. If the artificial valve 50 does not meet the requirements via evaluation, the locking position 30 of the valve locking device is not unlocked, and the valve can be pulled back into the sheath 44 by the valve locking device for complete withdrawal (as shown in FIG. 4), or be released again after adjustment. The diameter of the rod body 121 is smaller than that of the locking seat 11 and that of the guiding head 122, Therefore, when the artificial valve 50 is completely withdrawn, enough space can be reserved for the artificial valve 50.

In this embodiment, the artificial valve 50 can be pre-released at full-height, so that doctors can fully evaluate the artificial valve 50, and the artificial valve 50 can be completely withdrawn to facilitate implantation.

Embodiment II

As shown in FIG. 8 and FIG. 9, the locking seat 11 is provided with clamping recesses corresponding to the clamping protrusions 221. The clamping recesses match the clamping protrusions 221. In the embodiment, the locking seat 11 is provided with clamping bulging teeth 15, which are provided with a plurality of grooves 151. The clamping body 22 is provided with six finger-shaped clamping protrusions 221, three of which are longer and the remaining three are shorter. When locking, the three longer clamping protrusions 221 are clamped on the locking ends 611 of the artificial valve 50, and the second locking member 20 is moved axially, so that the finger-shaped clamping protrusions 221 are clamped into the grooves 151 so as to lock the locking ends 611 of the artificial valve 50.

Embodiment III

As shown in FIG. 10 and FIG. 11, in this embodiment, the rear end of the locking seat 11 is provided with a rear seat body 16, by which the locking ends 611 of the artificial valve 50 are further limited, and thereby achieving more accurate control of valve position.

Embodiment IV

As shown in FIG. 12 and FIG. 13, in this embodiment, the locking seat 11 is provided with clamping recesses corresponding to the clamping protrusions 221, wherein the clamping recesses match the clamping protrusions 221. In the embodiment, the locking seat 11 is provided with perforations 14. The clamping body 22 is provided with six finger-shaped clamping protrusions 221, three of which are longer and the remaining three are shorter. When locking, the three longer clamping protrusions 221 are clamped on the locking ends 611 of the artificial valve 50, and the second locking member 20 is moved axially, so that the finger-shaped clamping protrusions 221 are clamped into the perforations 14 to lock the locking ends 611 of the artificial valve 50.

Embodiment V

As shown in FIG. 14 and FIG. 15, in this embodiment, the locking seat 11 is provided with a placement recess 17. The locking ends 611 of the artificial valve 50 are locked within the placement recess 17, and the second locking member 20 is moved axially to lock the locking ends 611 of the artificial valve 50 through the limitation of the inner wall of the clamping body 22; when the second locking member 20 is moved in the opposite direction, the locking ends 611 of the artificial valve 50 are disengaged from the placement recess 17, and thereby the artificial valve 50 is unlocked.

Embodiment VI

As shown in FIG. 16 to FIG. 19, in this embodiment, the locking seat 11 is provided with clamping protrusions 221. As shown in FIG. 17, the clamping protrusions 221 match the inner wall of the clamping body 22 of the second locking member 20. The locking ends 611 of the artificial valve 50 are provided with locking holes 6111, and the clamping protrusions 221 are clamped in the locking holes 6111 to lock the locking ends 611. As shown in FIG. 18, when the second locking member 20 is moved axially relative to the first locking member 10, the locking ends 611 are disengaged from the clamping protrusion 221 and unlocked.

Embodiment VII

As shown in FIG. 20 to FIG. 30, the artificial valve 50 of this embodiment includes a top stent 60, a middle stent 70 and a bottom stent 80. The top stent 60, the middle stent 70 and the bottom stent 80 are connected in sequence. The top stent 60 is circumferentially provided with at least three locking stents 61. Each locking stent 61 has a locking end 611 at the top end. The middle stent 70 is provided with at least three valve leaflet fixing parts. In unlocked state of each locking end 611, the artificial valve is in a completely released state, and the diameter of the circumference where the uppermost edges of the three valve leaflet fixing parts are located is Φ1, and in a locked state of each locking end 611, the artificial valve is in an full-height pre-released state, and the diameter of the circumference where the uppermost edges of the three valve leaflet fixing parts are located is Φ2, which is 74% to 120% of Φ1. The comparison is as shown in FIG. 27 to FIG. 30.

In the unlocked state, the diameter of the circumference where the uppermost edges of the three valve leaflet fixing parts are located is Φ1, and the valve is in complete working state at the moment. In the locked state, when the artificial valve 50 is implanted (the locking ends 611 of the locking stent 61 are locked together), the diameter of the circumference where the uppermost edges of the three valve leaflet fixing parts are located is Φ2, and at this moment, Φ2 is 74% to 120% of Φ1, which can ensure that the valve can reach a basic working state in the locked state, so that doctors can pre-determine the working condition of the implanted valve, so as to better determine the direction of subsequent adjustment of the implantation plan without completely unlocking to release the artificial valve 50. When the artificial valve 50 does not meet the requirements, the artificial valve 50 can be withdrawn conveniently.

In this embodiment, a design range of Φ2 is 74% to 120% of Φ1, and the main considerations are as follows:

In the locked state of each locking end 611, the diameter Φ2 of the circumference where the uppermost edges of the three valve leaflet fixing parts are located determines the working condition of the artificial valve during pre-evaluation. If Φ2 is too small, three valve leaflets 93 will not fit smoothly, and will cause reflux; if Φ2 is too large, the free edges of the three valve leaflets 93 will not fit each other and the valve will not close tightly, which may also cause reflux.

During ventricular diastole, the volume of the ventricle increases, and the blood in the aorta tends to flow back to the ventricle. Because of the action of the blood flow, the valve leaflets 93 will close to prevent reflux of blood, and correspondingly, the blood will exert an acting force on the valve, causing suture rods 71 to deform inwardly. The deformation amount of the suture rods 71 is one of the determining factors for whether the valve fits well when the valve is closed. Therefore, when the size of Φ2 is considered, the deformation amount of suture rods 71 caused by the blood flow must be considered at the same time.

The deformation amount of the suture rods 71 is determined by factors such as patient's blood pressure, the structural stiffness of the suture rods, the size of the valve and the like. According to experience, under the action of blood flow, the deformation range of a single suture rod 71 is about 2% to 10% of According to the values above, and considering the deformation of three suture rods 71, when Φ2 of the three valve leaflets fixing part in locked state is 120% of Φ1 in unlocked state, the valve leaflets 93 may still work normally under the action of blood flow, so 120% of Φ1 is used as an upper limit of Φ2.

On the other hand, because of the good flexibility of the valve leaflets 93, the free edge of each valve leaflet 93 can still fit well even if the diameter of the circumference where the three valve leaflets fixing part are located is relatively small. According to experience, when the diameter of the circumference where the uppermost edges of the three valve leaflet fixing parts are located is 70% of Φ1 in unlocked state, the valve leaflets 93 may still close well. According to the conclusion that the minimum deformation of a single suture rod 71 can reach 2% of Φ1, and considering the three suture rods 71, when Φ2 of the three valve leaflet fixing parts in locked state is 74% of Φ1 of the three valve leaflet fixing parts in unlocked state, with the help of the compliance of the valve leaflets 93, the valve may still fit well and work normally. Therefore, 74% of is used as a lower limit of Φ2.

The optimal ratio of the diameter Φ2 to Φ1 of the circumference where the uppermost edges of the three valve leaflet fixing parts are located ranges from 85% to 110%. Within this range of ratios, the three valve leaflets close well in locked state, so that the function of the released valve can be accurately predicted.

The artificial valve 50 can be used in combination with the valve delivery device or the valve locking device described in the foregoing embodiments, as shown in FIG. 3, FIG. 6, FIG. 7, FIG. 9, FIG. 11 and FIG. 13.

Further, the middle stent 70 is provided with an anchoring frame 73 protruding circumferentially and facing the direction of the bottom stent 80. The anchoring frame 73 can assist the positioning of the artificial valve 50 at the root of the aorta 91, reducing the radial force of the bottom stent 80, and reducing the impact of the artificial valve 50 on the electrocardiographic conduction after implantation, thereby reducing the implantation rate of pacemaker after surgery.

The middle stent 70 includes suture rods 71 and connection rods 72. The suture rods 71 are the valve leaflet fixing parts, where a plurality of valve leaflet fixing holes 711 are provided for suturing and fixing the valve leaflets 93. The connection rods 72 are formed by multiple bifurcations at the lower ends of the suture rods 71. The lower portion of the middle stent 70 and the bottom stent 80 are of a grid structure. The anchoring frame 73 includes left and right side stent, and each side stent is provided with a fixed section 731 and a free section 732; the upper ends of the two fixed sections 731 are connected to the connection rods 72 on both sides, and the ends of the two free sections 732 are connected to each other. The fixed sections 731 protrude circumferentially outward relative to the connection rods 72, and the free sections 732 bend circumferentially inward relative to the fixed sections 731. The bent portions of the fixed sections 731 and the free sections 732 form anchoring protrusions 733. The anchoring frame 73 includes left and right side stents, and this structure enables reliable anchoring and has good stability. Through different bending directions of the fixed sections 731 and the free sections 732, the anchoring frame 73 has good flexibility, which is convenient for implantation and withdrawal, and can realize repeated positioning. After the positioning is completed, if the artificial valve moves longitudinally, the fixed sections 731 can attach to the inner wall of the aorta 91 and be blocked and limited; and the free sections 732 can attach to the inner wall of the aorta 91, and be blocked and limited by the autogenous valve 92.

The ends of the two free sections 732 are connected to form an end socket 7321, where a perforation 7322 is formed. According to needs, a protective sleeve 74 can be arranged on the perforation 7322, and the protective sleeve 74 can be made of soft tissue material or polymer material, which can reduce the risk of the anchoring frame 73 damaging the autogenous valve 92 or the valve leaflets 93 of the artificial valve 50. A developing positioning piece 75 may also be installed inside the perforation 7322, and the developing positioning piece 75 needs to be made of a material with good X-ray development property.

In order to satisfy the characteristics of the artificial valve 50 in the pre-released state, the top stent 60 can adopt a smaller structural stiffness than that of the middle stent 70, and specifically the following methods can be adopted.

1. The elastic modulus of the material of the top stent 60 is smaller than that of the middle stent 70.
2. The overall length of the top stent 60 is increased, so that the locking ends 611 are far away from the suture rods. Since the suture rods are the fixed ends of the locking ends, the stiffness of the locking ends can be reduced by increasing the overall length of the top stent 60.

3. The top stent 60 and the middle stent 70 are made of the same material to reduce the processing cost and ensure the overall mechanical strength. The top stent 60, the middle stent 70 and the bottom stent 80 are all made of nickel-titanium alloy material. Under this condition, the cross-section area of the rod-shaped material of the top stent 60 is smaller than that of the rod-shaped material of the middle stent 70, and preferably, the maximum value of the cross-sectional area of the rod-shaped material of the top stent 60 is 33% to 95% of the minimum value of the cross-sectional area of the middle stent 70 within the height range. The cross-section is perpendicular to the central axis of the whole valve. When the maximum cross-sectional area of the top stent within the height range is 50% to 90% of the minimum cross-sectional area of the middle stent within the height range, the structural stiffness of the locking ends and the structural stiffness of the suture rods of the middle stent can achieve a better ratio.

The top stent 60 generally includes three or six locking stents 61. When there are three locking stents 61, the structural stiffness of the locking end of each locking stents 61 is 5% to 50% of the structural stiffness of the suture rods of the middle stent 70. When there are six locking stents 61, the structural stiffness of the locking end of each locking stents 61 is 3% to 45% of the structural stiffness of the suture rods of the middle stent 70. When the structural stiffness of the locking ends of the locking stents 61 is between 20% and 40% of the structural stiffness of the suture rods of the middle stent 70, the diameter 12 of the circumference where the uppermost edges of the three valve leaflet fixing parts are located in locked state is 85% to 110% of the diameter Φ1 of the circumference where the uppermost edges of the three valve leaflet fixing parts are located in completely released state. Within this ratio range, the three valve leaflets close well in locked state, so that the valve function after being released can be accurately estimated.

The circumferential diameter of the bottom stent 80 gradually increases toward the bottom direction to form a trumpet shape, which can produce a greater radial compression after the artificial valve 50 is implanted, preventing the artificial valve 50 from shifting during work. The bottom stent 80 is provided with a circumferential skirt 81, which can be made of pericardium material or polymer material.

In this embodiment, a test method of the structural stiffness of a single locking end 611 is as follows, and as shown in FIG. 29, FIG. 30 and FIG. 31: a valve stent is released into a silicone tube 942 at ambient temperature of 37° C., and the inner diameter of the silicone tube 942 is selected to be within the diameter range of a human aortic valve ring applicable to the artificial valve. The silicone tube 942 is fixed on the platform of a universal tensile tester by a fixture 943, wherein the inner diameter of the fixture 943 matches the inner diameter of the silicone tube 942. The locking end 611 of the valve stent is tied with a guy wire 944 and is locked with a tensile tester clamp 941, so that the locking end 611 to be measured is centered by the tensile tester clamp 941, that is, the guy wire 944 is kept in a vertical direction. After the universal tensile tester is initially zeroed, the tensile tester clamp is operated to keep the locking end 611 in an undeformed state and the guy wire 944 is just stretched straight; this position is set as a zero point, the force value and deformation of the universal tensile tester are adjusted to zero; the force value under the upward tension of 10 mm displacement is tested, and the ratio of the maximum force value to the displacement is used as the structural stiffness.

The test method of the structural stiffness of a single suture rod is the same as above, as shown in FIG. 32, FIG. 33 and FIG. 34.

Embodiment VIII

As shown in FIG. 35, in this embodiment, the locking end 611 of the artificial valve 50 has a different structure. The locking end 611 has a locking head 6112, and the inner dimension of the locking head 6112 is reduced to form a locking neck 6113.

Referring again to FIG. 14 and FIG. 15, during implantation or withdrawal, the locking seat 11 of the valve delivery device is provided with a placement recess 17, and the locking ends 611 of the artificial valve 50 are locked within the placement recess 17, and through the axial movement of the second locking member 20, the locking ends 611 of the artificial valve 50 are limited and locked by the inner wall of the clamping body 22; when the second locking member 20 moves in the opposite direction, the locking ends 611 of the artificial valve 50 are disengaged from the placement recess 17, thereby unlocking the artificial valve 50.

Embodiment IX

As shown in FIG. 36, in this embodiment, the locking end 611 of the artificial valve has a different structure. The locking end 611 is provided with a locking hole 6111.

Referring again to FIG. 16 to FIG. 19, in this embodiment, the locking seat 11 of the valve delivery device is provided with a clamping protrusion 221, which matches with the inner wall of the clamping body 22 of the second locking member 20. The locking end 611 of the artificial valve 50 is provided with a locking hole 6111, and the clamping protrusion 221 is clamped in the locking hole 6111 to lock the locking end 611. As shown in FIG. 18, when the second locking member 20 moves axially relative to the first locking member 10, the locking ends 611 are disengaged from the clamping protrusions 221 to be unlocked.

The purposes of the embodiments above are to exemplarily reproduce and deduce the technical solutions of the present disclosure, and to describe the technical solutions, purposes and effects of the present disclosure in a complete way, so as to make the public understand the disclosed contents of the present disclosure more thoroughly and comprehensively instead of limiting the protection scope of the present disclosure.

The embodiments above are not exhaustively illustrated based on the present disclosure. In addition, there can be a number of other embodiments not listed. Any replacement and improvement made without departing from the concept of the present disclosure fall within the protection scope of the present disclosure.

What is claimed is:

1. An artificial valve, comprising a top stent, a middle stent and a bottom stent, wherein the top stent, the middle stent and the bottom stent are connected in sequence; the top stent is circumferentially provided with at least three locking stents; each of the locking stents has a locking end at a top; the middle stent is provided with at least three valve leaflet fixing parts; in an unlocked state of the locking end, a diameter of a circumference where an uppermost edges of the three valve leaflet fixing parts are located is Φ1, and in a locked state of the locking end, the diameter of the circumference where the uppermost edges of the three valve leaflet fixing parts are located is Φ2; wherein Φ2 is larger than or equal to 74% of Φ1.

2. The artificial valve according to claim 1, wherein the middle stent is provided with an anchoring frame protruding circumferentially and facing towards the bottom stent.

3. The artificial valve according to claim 2, wherein the anchoring frame comprises fixed sections and free sections; the fixed sections protrude circumferentially outward relative to the middle stent; and the free sections bend circumferentially inward relative to the fixed sections.

4. The artificial valve according to claim 3, wherein the fixed sections comprise two fixed sections, the free sections comprise two free sections; upper ends of the two fixed sections are connected to the middle stent, and ends of the two free sections are connected to each other.

5. The artificial valve according to claim 4, wherein the ends of the two free sections are connected to form an end socket; a perforation is formed in the end socket.

6. The artificial valve according to claim 5, wherein the perforation is provided with a protective sleeve and/or a developing positioning piece.

7. The artificial valve according to claim 1, wherein Φ2 is 74% to 120% of Φ1.

8. The artificial valve according to claim 1, wherein structural stiffness of the top stent is smaller than structural stiffness of the middle stent.

9. The artificial valve according to claim 8, wherein the middle stent comprises three suture rods, which are the valve leaflet fixing parts; and a number of the locking stents is three, and a structural stiffness of the locking end of each of the locking stents is 5% to 50% of a structural stiffness of each of the suture rods.

10. The artificial valve according to claim 8, wherein the middle stent comprises three suture rods, which are the valve leaflet fixing parts; and a number of the locking stents is six, and a structural stiffness of the locking end of each of the locking stents is 3% to 45% of a structural stiffness of each of the suture rods.

11. The artificial valve according to claim 1, wherein the valve leaflet fixing parts are provided with a plurality of valve leaflet fixing holes.

12. The artificial valve according to claim 1, wherein a circumferential diameter of the bottom stent gradually increases toward the bottom to form a trumpet shape.

13. The artificial valve according to claim 1, wherein a circumferential skirt is arranged on the bottom stent.

14. An artificial valve, comprising a top stent, a middle stent and a bottom stent, wherein the top stent, the middle stent and the bottom stent are connected in sequence; the top stent is circumferentially provided with at least three locking stents, which have locking ends at top ends; the middle stent is provided with valve leaflet fixing parts, and structural stiffness of the top stent is smaller than structural stiffness of the middle stent, wherein the middle stent comprises three suture rods, which are the valve leaflet fixing parts; and a number of the locking stents is three, and a structural stiffness of a locking end of each of the locking stents is 5% to 50% of a structural stiffness of each of the suture rods.

15. The artificial valve according to claim 14, wherein the middle stent further comprises suture rods and connection rods; the locking stents, the suture rods, the connection rods and the bottom stent are connected in sequence to form an integrated structure; a maximum area of a cross section of the locking stent which is perpendicular to a central axis of the artificial valve is 20% to 50% of a minimum area of a cross section of the suture rod which is perpendicular to the central axis of the artificial valve.

16. An artificial valve, comprising a top stent, a middle stent and a bottom stent, wherein the top stent, the middle stent and the bottom stent are connected in sequence; the top stent is circumferentially provided with at least three locking stents, which have locking ends at top ends; the middle stent is provided with valve leaflet fixing parts; and the middle stent further comprises suture rods and connection rods; the locking stents, the suture rods, the connection rods and the bottom stent are connected in sequence to form an integrated structure; a maximum area of a cross section of the locking stent which is perpendicular to a central axis of the artificial valve is 20% to 50% of a minimum area of a cross section of the suture rod which is perpendicular to the central axis of the artificial valve.

17. A valve delivery system, comprising an artificial valve and a delivery device, wherein the artificial valve comprises a top stent, a middle stent and a bottom stent; the top stent, the middle stent and the bottom stent are connected in sequence; the top stent is circumferentially provided with at least three locking stents; each of the locking stents has a locking end at a top; the middle stent is provided with at least three valve leaflet fixing parts; and the delivery device comprises a first locking member, a second locking member and a sheath; the first locking member and the second locking member are relatively movable; the first locking member is provided with a first locking portion; the second locking member is provided with a second locking portion; a locking position is formed between the first locking portion and the second locking portion; an inner diameter of the sheath is larger than a radial dimension of the second locking member; the sheath is movably sleeved on the outside of the first locking member and the second locking member; and when the first locking member and the second locking member move relatively, the locking position is in an unlocked or a locked state; in the unlocked state of the locking end, a diameter of a circumference where uppermost edges of the three valve leaflet fixing parts are located is Φ1, and in the locked state of the locking end, the diameter of the circumference where the uppermost edges of the three valve leaflet fixing parts are located is Φ2, which is 74% to 120% of Φ1.

* * * * *